(12) United States Patent
Arnould

(10) Patent No.: US 7,125,906 B2
(45) Date of Patent: *Oct. 24, 2006

(54) INDOLE DERIVATIVES HAVING ANTI-ANGIOGENETIC ACTIVITY

(75) Inventor: Jean-Claude Arnould, Reims (FR)

(73) Assignee: AstraZeneca AB, Sodertalje (SE)

( * ) Notice: Subject to any disclaimer, the term of this patent is extended or adjusted under 35 U.S.C. 154(b) by 52 days.

This patent is subject to a terminal disclaimer.

(21) Appl. No.: 10/509,633

(22) PCT Filed: Mar. 31, 2003

(86) PCT No.: PCT/GB03/01405

§ 371 (c)(1), (2), (4) Date: Sep. 29, 2004

(87) PCT Pub. No.: WO03/082271

PCT Pub. Date: Oct. 9, 2003

(65) Prior Publication Data

US 2005/0159474 A1    Jul. 21, 2005

(30) Foreign Application Priority Data

Apr. 3, 2002 (EP) ................... 02290822

(51) Int. Cl.
C07F 9/02      (2006.01)
C07D 209/04    (2006.01)
A61K 31/404    (2006.01)

(52) U.S. Cl. .................. 514/415; 548/414; 548/505

(58) Field of Classification Search .............. None
See application file for complete search history.

(56) References Cited

U.S. PATENT DOCUMENTS

| | | | |
|---|---|---|---|
| 2,789,984 A | 4/1957 | Speeter | |
| 2,802,003 A | 8/1957 | Grogan et al. | |
| 2,849,454 A | 8/1958 | Szmuszkovicz | |
| 2,883,394 A | 4/1959 | Schindler | |
| 2,890,223 A | 6/1959 | Woolley et al. | |
| 2,984,670 A | 5/1961 | Szmuszkovicz et al. | |
| 2,991,291 A | 7/1961 | Szmuszkovicz | |
| 3,037,031 A | 5/1962 | Lewis | |
| 3,166,570 A | 1/1965 | Winthrop | |
| 3,168,526 A | 2/1965 | Heinzelman et al. | |
| 3,901,914 A | 8/1975 | Hannah | |
| 4,533,672 A * | 8/1985 | Eakin et al. ............. | 514/415 |
| 4,952,584 A | 8/1990 | Thompson et al. | |
| 5,424,329 A | 6/1995 | Boschelli et al. | |

FOREIGN PATENT DOCUMENTS

| | | |
|---|---|---|
| CH | 380129 | 9/1964 |
| CH | 402860 | 5/1966 |
| CH | 414639 | 12/1966 |
| EP | 0107963 B1 | 4/1987 |
| EP | 0393575 B1 | 3/1994 |
| EP | 0372962 B1 | 7/1994 |
| EP | 0708091 A1 | 4/1996 |
| EP | 1297833 A1 | 4/2003 |
| ES | 227606 | 3/1957 |
| FR | 1238756 | 2/1960 |
| FR | 1388973 | 2/1965 |
| GB | 770370 | 3/1957 |
| GB | 807620 | 1/1959 |
| GB | 832855 | 4/1960 |
| GB | 834028 | 5/1960 |
| GB | 839628 | 6/1960 |
| GB | 841524 | 7/1960 |
| GB | 869775 | 6/1961 |
| GB | 873777 | 7/1961 |
| GB | 886684 | 1/1962 |
| GB | 942548 | 11/1963 |
| GB | 1033253 | 6/1966 |
| JP | 200080295 A2 | 3/2000 |
| SU | 175967 | 10/1965 |
| WO | WO 94/14770 A1 | 7/1994 |
| WO | WO 98/39323 A1 | 9/1998 |
| WO | WO 99/12905 A1 | 3/1999 |

(Continued)

OTHER PUBLICATIONS

Sheppard, G, S. '3-(2-(3-Pyridinyl)thiazolidin-4-oyl)indoles, a novel series of platelet activating factor antagonists' *Journal Of Medicinal Chemistry* vol. 37, No. 13, 2011-2032, 1994.

(Continued)

*Primary Examiner*—Kamal A. Saeed
*Assistant Examiner*—Nyeemah Grazier

(57) ABSTRACT

The invention relates to the use of a compound of Formula (I), for the manufacture of a medicament to inhibit and/or reverse and/or alleviate symptoms of angiogenesis and/or any disease state associated with angiogenesis:

Formula (I)

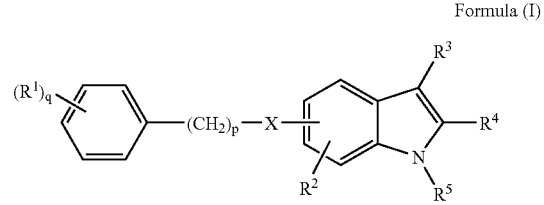

wherein: X, p, q, $R^1$, $R^2$, $R^3$, $R^4$, and $R^5$ are as defined in the description. The invention also related to use of compounds of Formula (I) as medicaments and also to novel compounds of Formula (I). The invention further provides pharmaceutical compositions of compounds of Formula (I) and processes for the synthesis of compounds of Formula (I).

13 Claims, No Drawings

FOREIGN PATENT DOCUMENTS

| | | |
|---|---|---|
| WO | WO 99/29660 A1 | 6/1999 |
| WO | WO 99/29661 A1 | 6/1999 |
| WO | WO 99/51598 A1 | 10/1999 |
| WO | WO 99/51600 A1 | 10/1999 |
| WO | WO 00/48606 A1 | 8/2000 |
| WO | WO 00/66585 A1 | 11/2000 |
| WO | WO 01/19794 A2 | 3/2001 |
| WO | WO 01/29025 A2 | 4/2001 |
| WO | WO 01/82909 A2 | 11/2001 |
| WO | WO 200182909 A2 * | 11/2001 |
| WO | WO 01/92224 A1 | 12/2001 |
| WO | WO 02/70478 A1 | 9/2002 |

OTHER PUBLICATIONS

Kwong, F, Y & Buchwald, S. L. 'A general, efficient, and inexpensive catalyst system for the coupling of aryl iodides and thiois' *Org. Lett.* vol. 4, No. 20, 3517-3520, 2002.

Database Crossfire Beilstein 'Beilstein institute zur foerdering der chemischen wissenschaften' Database Accession No. 8172403, 2000.

Database Crossfire Beilstein 'Beilstein institute zur foerdering der chemischen wissenschaften' Database Accession No. 183150, reaction 2 of 4, 1988.

Database Crossfire Beilstein 'Beilstein institute zur foerdering der chemischen wissenschaften' Database Accession No. 5433848, 1993.

Monge A et al 'New indole and pyridazinoindole analogs—synthesis and study as inhibitors of phosphodiesterases and as inhibitors of blood platelet aggregation' *Archiv Der Pharmazie* vol. 328, No. 10, pp. 689-698, 1995.

Aleksandrzak, K. McGown, A, T & Hadfield, J, A. 'Antimitotic activity of diaryl compounds with structural features resembling combretastatin A-4' *Anti-Cancer Drugs* vol. 9, 545-550, 1998.

McGown, A, T. & Fox, B, W. 'Structural and biochemical comparison of the anti-mitotic agents colchicines, combretastatin A4 and amphethinile' *Anti-Cancer Drug Design* vol. 3, pp. 249-254, 1989.

Galbraith, S. M et al. 'Effects of combrestatin A4 phosphate on endothelial cell morphology in vitro and relationship to tumour vascular targeting activity in vivo' *Anti-Cancer Research* vol. 21, pp. 93-102, 2001.

Bolton, D et al 'Synthesis and potential anxiolytic activity of 4-amino-pyrido[2,3-b]indoles' *Bioorganic & Medicinal Chemistry Letters* vol. 3, No. 10, pp. 1941-1946, 1993.

Blackburn, T,P. '11-amino-2,6-dimethyl-1,2,3,4-tetrahydro-6H-quinindolin-1-one, a novel $GABA_A$ modulator with Potential anxiolytic activity' *Bioorganic & Medicinal Chemistry Letters* vol. 4, No. 2, pp. 279-284, 1994.

McGown, A, T et al. 'Pre-clinical studies of a novel anti-mitotic agent, amphethinile' *Br J Cancer* vol. 57, pp. 157-159, 1988.

McGown, A, T. & Fox, B, W. 'Interaction of the novel agent amphethinile with tubulin' *Br J Cancer* vol. 59, pp. 865-868, 1989.

Newell, D, R et al 'Evaluation of rodent-only toxicology for early clinical trials with novel cancer therapeutics' *British Journal of Cancer* vol. 81(5), pp. 760-768, 1999.

Dark, G, G. 'Combretastatin A-4, an agent that displays potent and selective toxicity toward tumor vasculature' *Cancer Research* vol. 57, pp. 1829-1834, 1997.

Player, M, R & Sowell, J, W. 'Synthesis of 1,3-disubstituted-2-amino-5-hydroxyindoles by reductive aromatization' *J Heterocyclic Chem* vol. 30 (125), pp. 125-128, 1993.

Hess, S et al. '7-deazaadenines bearing polar substituents: structure-activity relationships of a new $A_1$ and $A_3$ adenosine receptor antagonists' *J Med Chem* vol. 43, pp. 4636-4646, 2000.

Fuse, E et al. 'Application of pharmacokinetically guided dose escalation with respect to cell cycle phase specificity' *Journal of the National Cancer Institute* vol. 86, No. 13, 1994.

Eger, K et al 'Synthesis of substituted indoles and pyrimido[4,5-b]indoles by dehydration of tetrahydroindoles and tetrahydropyrimidoindoles' *Liebigs Ann Chem* pp. 465-470, 1993.

Keglevic, D & Goles, D 'Indole compounds. VI. Syntheses of indole thioethers by direct cyclization of phenylhydrazine hydrochlorides and aliphatic acetals under mild conditions' *Croatica Chemica Acta* vol. 42, pp. 513-521, 1970.

Desaty, D et al 'The synthesis of N-acetylserotonin' *Biochem Biophys Acta* vol. 62, pp. 179-180, 1962.

Mashima, H & Matsumura, M. 'Roles of external ions in the excitation-contraction coupling of frog skeletal muscle' *Japan J. Physiol* vol. 12, pp 639-653, 1962.

Heath-Brown, B & Philpott, P. G. 'Studies in the indole series. Part 1. Indolylalkylamines' *J Chem Soc* pp. 7165-7078, 1965.

Desai, H. K. & Usgaonkar, R, N. 'Isocoumarins. Part 1. Synthesis of 4-Methylisocoumarins' *Jour Indian Chem Soc* vol. 41, No. 12, pp. 821-829, 1964.

Heacock, R, A. & Hutzinger, O. 'The preparation of the hydroxyskatoles and 5,6-dihydroxyskatole' *Canadian Journal of Chemistry* vol. 42, pp. 514-521, 1964.

Ma, J, C, N & Warnhoff, E, W. 'On the use of nuclear magnetic resonance for the detection, estimation and characterization of N-methyl groups' *Canadian Journal of Chemistry* vol. 43, pp. 1849-1869, 1965.

Benigni, J, D & Minnis, R, L. 'The synthesis of 5,6-dihydroxyindole and some of its derivatives (1)' *J Heterocyclic Chem* vol. 2, pp. 387-392, 1965.

Marchand, B et al 'Preparative chemistry of indole compounds. 1. Preparation of phenylhydrazones of pyruvic acid esters from methyloxalacetic esters and diazonium salts and conversion of these compounds into indole-2-carboxylic esters' *J Prakt Chem* vol. 13, pp. 54-57, 1961. +English Abstract.

Taborsky, R, G. & Delvigs, P. 'Synthesis of some substituted tryptophols of possible physiological importance and a study with 3-(2-acetoxyethyl)-5-methoxyindole (5-methoxytryptophol O-acetate) on sexual maturation' *J Med Chem* vol. 9, pp. 251-254, 1966.

Taborsky, R, G et al '6-hydroxyindoles and the metabolism of melatonin' *J. Med Chem* vol. 8(6), pp 855-858, 1965.

Taborsky, R, G et al. 'Synthesis and preliminary pharmacology of some 1-methylindoles' *J Med Chem* vol. 8(4), pp. 460-466, 1965.

Arutyunyan, G, S. et al 'Relations between chemical structure and pharmacological activity of 5-alkoxytryptamines' *Farmakol Toksikol* vol. 27(6), pp. 681-686, 1964. +English Abstract.

Shagalov, N, P. et al. 'Indole derivatives. XXI. Synthesis of 4- and 6-chloroindolybutyric acids' *Zh Obshch Khim* vol. 34(5), pp. 1592-1595, 1964. +English Abstract.

Keglevic, D et al 'The synthesis of 3,5-disubstituted indoles by cyclization under mild conditions' *Croat Chem Acta* vol. 33, pp. 83-88, 1961. +English Abstract.

Greenberg, A, J. & Ketcham, R 'Determination of urinary indolic metabolites' *Journal of Pharmaceutical Sciences* vol. 67(4), pp. 478-480, 1978.

Cotterill et al 'Cyclopropamitosenes, Novel Bioreductive Anticancer Agents. Synthesis, Electrochemistry, and Biological Activity of 7-Substituted Cyclopropamitosenes and Related Indolequinones' *J Med Chem* vol. 37(22), pp. 3834-3843, 1994.

Cotterill et al 'Cyclopropamitosenes, Novel Bioreductive Anticancer Agents. Synthesis, 7-Methoxycyclopropamitosene and Related Indolequinones', *Tetrahedron* vol. 50(25), pp. 7657-7674, 1994.

Moody et al 'Synthesis and Biological Activity of Thiazolylindolequinones, Analogues of the Natural Product BE 10988', *J Med Chem* vol. 38(6), pp. 1039-1043, 1995.

Moody et al 'Synthesis andCytotoxic of Thiazolyl Indolequinones', Anti-Cancer Drugs vol. 10, pp. 577-589, 1999.

Chikvaidze et al '*Soobshch Akad Nauk Gruz*' Bulletin of the Academy of Sciences of Georgia, vol 141(3), pp. 545-548, 1991. +English Abstract.

Beswick et al 'The Synthesis of 4—Substituted Indoles via Arenetricarbonylchromium(0) Complexes' *Tetrahedron* vol. 44(23), pp. 7325-7334, 1988.

Nechvatal & Widdowson 'A New Synthesis of 4-Substituted Indoles via Tricarbonylarenechromium(0) Complexes' *J Chem Soc Chem Commun* vol. 8, pp. 467-468, 1982.

Dickens et al 'Transition Metal Medicated Thiation of Aromatic Rings' *Tetrahdron* vol. 47(40), pp. 8621-8634, 1991.

Fukuda et al 'Directed C-7 Lithiation of 1-(2,2-Diethylbutanoyl)indoles' *Tetrahedron* vol. 58(30) pp. 9151-9162 1999.

Alexandrzak et al 'Antimitotic Activity of Diaryl Compounds with Structural Features Resembling Combretastatin A-4' *Anticancer Drugs* vol. 9(6), pp. 545-550, 1998.

McGowan & Fox 'Structural and Biochemical Comparison of the Anti-Mitotic Agents Colchicine, Combretastatin A4 and Amphelthinile' *Anticancer Drug Des* vol. 3(4), pp. 249-254,1989.

McGowan & Fox 'Interaction of the Novel Agent Amphethinile with Tubulin', *British Journal of Cancer* vol. 59(6), pp. 865-868, 1989.

McGowan & Fox 'Pre-Clinical Studies of a Novel Anti-Mitotic Agent, Amphethinile' *British Journal of Cancer* vol. 57(2), pp. 157-159, 1988.

Gairns et al 'Synthesis of Fused $1\lambda^\alpha$, 2-Thiazines(2-Azathiabenzenes)' *J Chem Soc Perkin Trans* vol. 1(3), pp. 483-489, 1986.

Allen 'Synthesis of Indole-2-Carboxylic Acid Esters', *Synth Commun* vol. 29(3), pp. 447-455, 1999.

Dunan & Andrako 'Synthesis of 2-(N,N-Dialkylaminomethyl)-7-Phenylthioindoles', *Pharm Sci* vol. 57(6), pp. 979-983, 1968.

Somei & Natsume 'Photochemical Rearrangements for the Synthesis of 3-,4- and 6- Substituted Indoles', *Tetrahedron Lett* vol. 27, pp. 2451-2454, 1973.

Mirziashvili et al *Khim Geterotsikl Soedin* vol. 1, pp. 54-56, 1991. +English Abstract.

Nerenberg et al 'Radioimmunoassay of Oxfendazole in Bovine, Equine, or Canine Plasma or Serum', *J Pharm Sci* vol. 67(11), pp. 1553-1557, 1978.

Chikvaidze et al 'New Indole Derivatives: Synthesis and Antibacterial Activity' *Pharmaceutical Chemistry Journal*, vol. 32, No. 1, pp. 30-33, 1998.

McCormick et al 'Characterization and Synthesis of a New Calcium Antagonist from the Venom of a Fishing Spider', *Tetrahedron Lett* vol. 49, No. 48, pp. 11155-11168, 1993.

Chikvaidze et al 'Indole Derivatives 138.* Synthesis of Some New Sulfur-Containing Derivatives of Indole', *Chem Heterocycl Compd*, vol 27 No. 11 pp. 1218-1221, 1991.

* cited by examiner

INDOLE DERIVATIVES HAVING ANTI-ANGIOGENETIC ACTIVITY

This application is a national stage filing under 35 U.S.C. 371 of International Application No. PCT/GB03/01405, filed Mar. 31, 2003, which claims priority from European Patent Application No. 02290822.2, filed Apr. 3, 2002, the specification of which is incorporated by reference herein. International Application No. PCT/GB03/01405 was published under PCT Article 21(2) in English.

This invention relates to vascular damaging agents and their uses. In particular it relates to certain compounds which may be of use as vascular damaging agents, to methods for preparing the compounds, to their use as medicaments (including methods for the treatment of angiogenesis or disease states associated with angiogenesis) and to pharmaceutical compositions containing them. The invention also relates to the use of such compounds in the manufacture of medicaments for the production of anti-angiogenic and/or anti-vascular effects.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57–66; Folkman, 1995, Nature Medicine 1: 27–31). Formation of new vasculature by angiogenesis is a key pathological feature of several diseases (J. Folkman, New England Journal of Medicine 333, 1757–1763 (1995)). For example, for a solid tumour to grow it must develop its own blood supply upon which it depends critically for the provision of oxygen and nutrients; if this blood supply is mechanically shut off the tumour undergoes necrotic death. Neovascularisation is also a clinical feature of skin lesions in psoriasis, of the invasive pannus in the joints of rheumatoid arthritis patients and of atherosclerotic plaques. Retinal neovascularisation is pathological in macular degeneration and in diabetic retinopathy.

Reversal of neovascularisation by damaging the newly-formed vascular endothelium is therefore expected to have a beneficial therapeutic effect. Such vascular-damaging activity would clearly be of value in the treatment of disease states associated with angiogenesis such as cancer, diabetes, psoriasis, rheumatoid arthritis, Kaposi's sarcoma, haemangioma, acute and chronic nephropathies, atheroma, arterial restenosis, autoimmune diseases, acute inflammation, endometriosis, dysfunctional uterine bleeding and ocular diseases with retinal vessel proliferation.

Certain known compounds that cause selective destruction of tumour vasculature have been reported, in vitro and at non-cytotoxic concentrations, to cause effects on proliferating endothelial cells, ie, cell detachment [Blakey D C et al, *Proceedings of the American Association for Cancer Research*, 41, 329, 2000 abstract 2086] and changes in cell shape [Davis P D et al, *Proceedings of the American Association for Cancer Research*, 41, 329, 2000 abstract 2085; Chaplin D J & Dougherty G J, *Br J Cancer*, 80, Suppl 1, 57–64, 1999]. It can therefore be expected that these compounds will have damaging effects on newly-formed vasculature, for example the vasculature of tumours. It can reasonably be predicted, for example, that they will be capable of causing selective destruction of tumour vasculature, both in vitro and in vivo. Destruction of tumour vasculature in turn leads to a reduction in tumour blood flow and to tumour cell death due to starvation of oxygen and nutrients, ie, to anti-tumour activity [Davis P D et al; Chaplin D J & Dougherty G J; Blakey D C et al, all supra].

Compounds with this activity have also been described in International Patent Application WO 99/02166 (Angiogene Pharmaceuticals), International Patent Application WO00/40529 (Angiogene Pharmaceuticals) and International Patent Application WO 00/41669 (Angiogene Pharmaceuticals).

We have identified a class of indole compounds with vascular damaging activity. Thus, according to the first feature of the present invention there is provided the use of a compound of Formula (I), for the manufacture of a medicament to inhibit and/or reverse and/or alleviate symptoms of angiogenesis and/or any disease state associated with angiogenesis Formula (I)

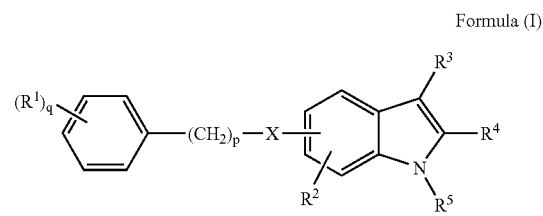

wherein:

$R^1$ is independently selected from halo, hydroxy, amino, alkanoylamino, —OPO$_3$H$_2$, or C$_{1-4}$alkoxy, wherein the amino group is optionally substituted by an amino acid residue and the hydroxy group is optionally esterified;

X is selected from: —O—, —S—, —SO— or —SO$_2$—;

$R^2$ is selected from: hydrogen, C$_{1-4}$alkyl or C$_{1-4}$alkoxy;

$R^3$ and $R^4$ are independently selected from: hydrogen, C$_{1-4}$alkyl, C$_{1-4}$alkanoyl, C$_{1-4}$alkoxycarbonyl, C$_{1-4}$alkoxycarbonylC$_{1-4}$alkyl, C$_{1-4}$alkoxycarbonylamino, amino, aminoC$_{1-4}$alkyl, carbamoyl, carbamoylC$_{1-4}$alkyl, cyano, cyanoC$_{1-4}$alkyl, hydroxy, hydroxyC$_{1-4}$alkyl, or a group of Formula (II):

Formula (II)

$R^6$ is hydrogen or C$_{1-4}$alkyl;

$R^5$ and $R^7$ are independently selected from hydrogen, C$_{1-4}$alkyl or a group of Formula (III):

Formula (III)

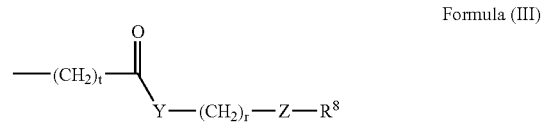

wherein Y is selected from —NH—, —O— or a bond;

Z is selected from —NH—, —O—, —C(O)— or a bond;

r is an integer from 0 to 4;

t is an integer from 0 to 1;

$R^8$ is hydrogen, C$_{1-4}$alkyl, C$_{1-4}$alkoxy, aryl, 5 or 6 membered heterocyclyl, 5- or 6-membered heteroaryl, wherein aryl, heteroaryl or heterocyclyl are optionally substituted by $C_{1-4}$alkyl, $C_{1-4}$alkoxy, or a group of Formula (IV):

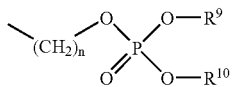
Formula (IV)

wherein n is an integer from 1 to 6, and;
$R^9$ and $R^{10}$ are independently selected from hydrogen, $C_{1-4}$alkyl or aryl; and
p is an integer from 0 to 1; and
q is an integer from 0 to 3;

with the proviso that:
(i) when $R^3$ is cyano then $R^4$ cannot be a group of Formula (II), and
(ii) when q is 0, $R^3$ is cyano and X is —S— then $R^4$ is other than amino;
or a salt, pro-drug or solvate thereof.

According to a further aspect of the first feature of the invention there is provided the use of a compound of Formula (Ia), for the manufacture of a medicament to inhibit and/or reverse and/or alleviate symptoms of angiogenesis and/or any disease state associated with angiogenesis:

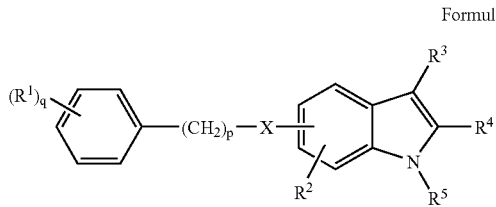
Formula (Ia)

wherein:
$R^1$ is independently selected from hydroxy, amino, alkanoylamino, —OPO$_3$H$_2$, or $C_{1-4}$alkoxy, wherein the amino group is optionally substituted by an amino acid residue and the hydroxy group is optionally esterified;
wherein: X, p, q, $R^2$, $R^3$, $R^4$, and $R^5$ are as defined for Formula (I) above;

with the proviso that:
(i) when $R^3$ is cyano then $R^4$ cannot be a group of Formula (II), and or a salt, pro-drug or solvate thereof.

According to a further aspect of the first feature of the invention there is provided a method of treatment, in a warm-blooded animal, to inhibit and/or reverse and/or alleviate symptoms of angiogenesis and/or any disease state associated with angiogenesis comprising administering to said warm-blooded animal a therapeutically (including prophylactically) effective amount of a compound of Formula (I) or Formula (Ia), or a pharmaceutically acceptable salt, pro-drug or solvate thereof.

Preferably a warm-blooded animal is a human.

A further feature of the invention provides a group of indole compounds for use in medicine. Thus, according to a second feature of the present invention there is provided the use of a compound of Formula (V) as a medicament, wherein:

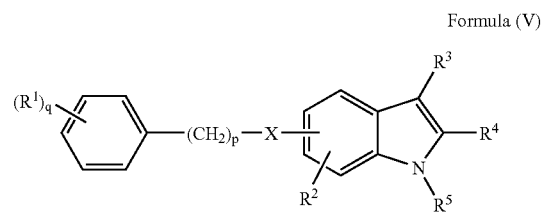
Formula (V)

$R^1$ is independently selected from halo, hydroxy, amino, alkanoylamino, —OPO$_3$H$_2$, or $C_{1-4}$alkoxy, wherein the amino group is optionally substituted by an amino acid residue and the hydroxy group is optionally esterified;
X is selected from: —O—, —S—, —SO— or —SO$_2$—;
$R^2$ is selected from: hydrogen, $C_{1-4}$alkyl or $C_{1-4}$alkoxy;
$R^3$ and $R^4$ are independently selected from: hydrogen, $C_{1-4}$alkyl, $C_{1-4}$alkanoyl, $C_{1-4}$alkoxycarbonyl, $C_{1-4}$alkoxycarbonyl$C_{1-4}$alkyl, $C_{1-4}$alkoxycarbonylamino, amino, amino$C_{1-4}$alkyl, carbamoyl, carbamoyl$C_{1-4}$alkyl, cyano, cyano$C_{1-4}$alkyl, hydroxy, hydroxy$C_{1-4}$alkyl; or a group of Formula (II):

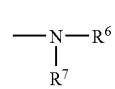
Formula (II)

$R^6$ is hydrogen or $C_{1-4}$alkyl;
$R^5$ and $R^7$ are independently selected from hydrogen, $C_{1-4}$alkyl or a group of Formula (III):

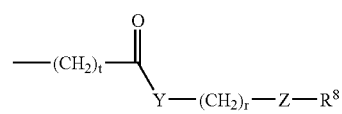
Formula (III)

wherein Y is selected from —NH—, —O— or a bond;
Z is selected from —NH—, —O—, —C(O)— or a bond;
r is an integer from 0 to 4;
t is an integer from 0 to 1;
$R^8$ is hydrogen, $C_{1-4}$alkyl, $C_{1-4}$alkoxy, aryl, 5 or 6 membered heterocyclyl, 5- or 6-membered heteroaryl, wherein aryl, heteroaryl or heterocyclyl is optionally substituted by $C_{1-4}$alkyl or $C_{1-4}$alkoxy, or a group of Formula (IV):

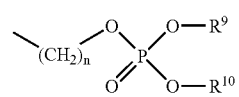
Formula (IV)

wherein n is an integer of from 1 to 6, and;
$R^9$ and $R^{10}$ are independently selected from hydrogen or $C_4$alkyl or aryl; and
p is an integer from 0 to 1; and
q is an integer from 0 to 3, preferably from 1 to 3;

with the proviso that
(i) when $R^3$ is cyano then $R^4$ cannot be a group of Formula (II);

(ii) when q is 0 and X is —S— then $R^3$ is other than cyano;
(iii) when q is 0, p is 1, $R^2$ is hydrogen or 5-methoxy, $R^3$ is cyanomethyl and $R^4$ is hydrogen or $R^3$ is hydrogen and $R^4$ is cyanomethyl then $R^5$ cannot be hydrogen methyl or acetyl;
(iv) when $(R^1)_q$ is 4-methoxy, 4-amino or 3,4,5-trimethoxy, p is 0 or 1, $R^2$ is hydrogen or 5-methoxy, $R^3$ is hydrogen, cyanomethyl or 2-aminoethyl, $R^4$ is hydrogen or ethoxycarbonyl then $R^5$ cannot be hydrogen or methyl;
(v) when q is 0, p is 0 or 1, $R^2$ is hydrogen, 7-methyl, 5-methoxy or 6-methoxy, $R^3$ is aminomethyl, 2-aminoethyl, 2-aminopropyl or 2-aminobutyl, $R^4$ is hydrogen or methyl, then $R^5$ cannot be hydrogen, methyl, n-butyl or acetyl;
(vi) when q is 0, p is 0 or 1, $R^2$ is hydrogen, $R^3$ is methyl, ethyl, hydroxy, hydroxymethyl, 2-hydroxyethyl or 1-methylethoxy, $R^4$ is hydrogen, methyl, ethoxycarbonyl or tert-butoxycarbonyl or carbamoyl, then $R^5$ cannot be hydrogen, methyl or acetyl;
(vii) when q is 0, p is 0 or 1, $R^2$ is hydrogen or 5-methoxy, $R^3$ is hydrogen or bromo, $R^4$ is hydrogen, methyl, methoxycarbonyl, ethoxycarbonyl, tert-butoxycarbonyl or hydroxymethyl then $R^5$ cannot be methyl or n-butyl; and
(viii) when q is 0, p is 1, $R^2$ is hydrogen, 6-methyl, 7-methyl, or 5-methoxy, $R^3$ is hydrogen, $R^4$ is hydrogen, methoxycarbonyl, ethoxycarbonyl, or 2-aminoethyl, then $R^5$ cannot be hydrogen;

or a salt, pro-drug or solvate thereof;

According to a further aspect of the second feature of the invention there is provided a pharmaceutical composition comprising a compound of Formula (V) or pharmaceutically-acceptable salt, pro-drug or solvate thereof.

According to a further aspect of the second feature of the invention there is provided a pharmaceutical composition comprising a compound of Formula (V), or a pharmaceutically-acceptable salt, pro-drug or solvate thereof, in admixture with a pharmaceutically-acceptable diluent or carrier.

The invention also provides a novel group of indole compounds. Thus, according to a third feature of the invention there is provided a compound of Formula (VI)

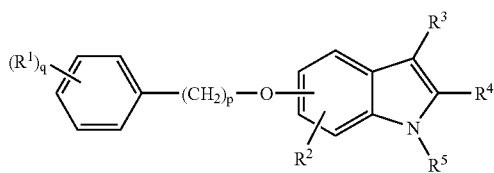

Formula (VI)

wherein:
$R^1$ is independently selected from halo, hydroxy, amino, alkanoylamino, —$OPO_3H_2$, or $C_{1-4}$alkoxy, wherein the amino group is optionally substituted by an amino acid residue and the hydroxy group is optionally esterified;
$R^2$ is selected from: hydrogen, $C_{1-4}$alkyl or $C_{1-4}$alkoxy;
$R^3$ and $R^4$ are independently selected from: hydrogen, $C_{1-4}$alkyl, $C_{1-4}$alkanoyl, $C_{1-4}$alkoxycarbonyl, $C_4$alkoxycarbonyl$C_{1-4}$alkyl, $C_{1-4}$alkoxycarbonylamino, amino, amino$C_{1-4}$alkyl, carbamoyl, carbamoyl$C_{1-4}$alkyl, cyano, cyano$C_{1-4}$alkyl, hydroxy, hydroxy$C_{1-4}$alkyl; or a group of Formula (II):

Formula (II)

$R^6$ is hydrogen or $C_{1-4}$alkyl;
$R^5$ and $R^7$ are independently selected from hydrogen, $C_{1-4}$alkyl or a group of Formula (III):

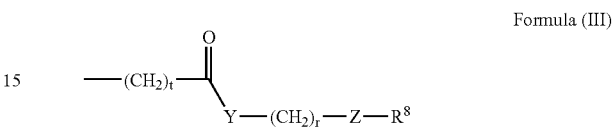

Formula (III)

wherein Y is selected from —NH—, —O— or a bond;
Z is selected from —NH—, —O—, —C(O)— or a bond;
r is an integer from 0 to 4;
t is an integer from 0 to 1;
$R^8$ is hydrogen, $C_{1-4}$alkyl, $C_{1-4}$alkoxy, aryl, 5 or 6 membered heterocyclyl, 5- or 6-membered heteroaryl, wherein aryl, heteroaryl or heterocyclyl is optionally substituted by $C_{1-4}$alkyl or $C_{1-4}$alkoxy, or a group of Formula (IV):

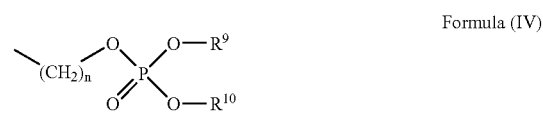

Formula (IV)

wherein n is an integer of from 1 to 6, and;
$R^9$ and $R^{10}$ are independently selected from hydrogen or $C_{1-4}$alkyl or aryl; and
p is an integer from 0 to 1; and
q is an integer from 0 to 3, preferably from 1 to 3;

with the proviso that
(i) when $R^3$ is cyano then $R^4$ cannot be a group of Formula (II);
(ii) when q is 0, p is 1, $R^2$ is hydrogen or 5-methoxy, $R^3$ is cyanomethyl and $R^4$ is hydrogen or $R^3$ is hydrogen and $R^4$ is cyanomethyl then $R^5$ cannot be hydrogen methyl or acetyl;
(iii) when $(R^1)_q$ is 4-methoxy, 4-amino, or 3,4,5-trimethoxy, p is 0 or 1, $R^2$ is hydrogen or 5-methoxy, $R^3$ is hydrogen, cyanomethyl or 2-aminoethyl, $R^4$ is hydrogen or ethoxycarbonyl then $R^5$ cannot be hydrogen or methyl;
(iv) when q is 0, p is 0 or 1, $R^2$ is hydrogen, 7-methyl, 5-methoxy or 6-methoxy, $R^3$ is aminomethyl, 2-aminoethyl, 2-aminopropyl or 2-aminobutyl, $R^4$ is hydrogen or methyl, then $R^5$ cannot be hydrogen, methyl, n-butyl or acetyl;
(v) when q is 0, p is 1, $R^2$ is hydrogen, $R^3$ is methyl, ethyl, hydroxy, hydroxymethyl, 2-hydroxyethyl or 1-methylethoxy, $R^4$ is hydrogen, methyl, ethoxycarbonyl or tert-butoxycarbonyl or carbamoyl, then $R^5$ cannot be hydrogen, methyl or acetyl;
(vi) when q is 0, p is 1, $R^2$ is hydrogen or 5-methoxy, $R^3$ is hydrogen or bromo, $R^4$ is hydrogen, methyl, methoxycarbonyl, ethoxycarbonyl, tert-butoxycarbonyl or hydroxymethyl then $R^5$ cannot be methyl or n-butyl; and (vii) when q is 0, p is 1, $R^2$ is hydrogen, 6-methyl, 7-methyl, or 5-methoxy, $R^3$ is hydrogen, $R^4$ is methoxycarbonyl, ethoxycarbonyl, or 2-aminoethyl, then $R^5$ cannot be hydrogen;

or a salt, pro-drug or solvate thereof;

According to a further aspect of the third feature of the invention there is provided a compound of Formula (VIa)

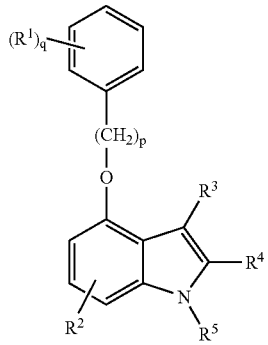

Formula (VIa)

wherein: p, q, $R^1$, $R^2$, $R^3$, $R^4$, and $R^5$ are as defined for Formula (VI) above with the proviso that (i) when $R^3$ is cyano then $R^4$ cannot be a group of Formula (II);

(ii) when q is 0, p is 1, $R^2$ is hydrogen or 5-methoxy, $R^3$ is cyanomethyl and $R^4$ is hydrogen or $R^3$ is hydrogen and $R^4$ is cyanomethyl then $R^5$ cannot be hydrogen;

(iii) when q is 0, p is 1, $R^2$ is hydrogen or 5-methoxy, $R^3$ is aminomethyl, 2-aminoethyl, 2-aminopropyl, 2-aminobutyl, methoxycarbonyl or methyl, $R^4$ is hydrogen or methyl, then $R^5$ cannot be hydrogen, methyl or n-butyl; and (iv) when q is 0, p is 1, 2 is hydrogen or 5-methoxy, $R^3$ is hydrogen, $R^4$ is hydrogen, methyl, hydroxymethyl or methoxycarbonyl then $R^5$ cannot be hydrogen, methyl or n-butyl.

or a salt, pro-drug or solvate thereof;

According to a further aspect of the third feature of the invention there is provided a compound of Formula (VIb)

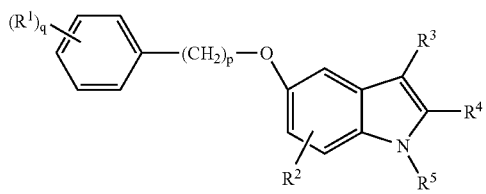

Formula (VIb)

wherein: p, q, $R^1$, $R^2$, $R^3$, $R^4$, and $R^5$ are as defined for Formula (VI) above with the proviso that (i) when $R^3$ is cyano then $R^4$ cannot be a group of Formula (II);

(ii) when $(R^1)_q$ is 4-methoxy, p is 0, $R^2$ is hydrogen, $R^3$ is hydrogen, cyanomethyl or 2-aminoethyl $R^4$ is hydrogen or ethoxycarbonyl, then $R^5$ cannot be hydrogen;

(iii) when q is 0, p is 1, $R^2$ is hydrogen, $R^3$ is cyanomethyl and $R^4$ is hydrogen or $R^3$ is hydrogen and $R^4$ is cyanomethyl then $R^5$ cannot be hydrogen, methyl or acetyl;

(iv) when q is 0, p is 0 or 1, $R^2$ is hydrogen, 6-methoxy or 7-methyl, $R^3$ is 2-aminoethyl or 2-aminopropyl, $R^4$ is hydrogen or methyl, then $R^5$ cannot be hydrogen, methyl or acetyl;

(v) when q is 0, p is 1, $R^2$ is hydrogen, $R^3$ is methyl, ethyl, bromo, hydroxy, hydroxymethyl, 2-hydroxyethyl, 1-methylethoxy, acetyl, ethoxycarbonyl or ethoxycarbonylethyl, $R^4$ is hydrogen, methyl, carbamoyl, ethoxycarbonyl or tert-butoxycarbonyl, then $R^5$ cannot be hydrogen or methyl; and (vi) when q is 0, $R^1$ is hydrogen, p is 1, $R^2$ is hydrogen, 6-methyl or 7-methyl, $R^3$ is hydrogen, $R^4$ is hydrogen, ethoxycarbonyl or 2-aminoethyl, then $R^5$ cannot be hydrogen or methyl;

or a salt, pro-drug or solvate thereof;

According to a further aspect of the third feature of the invention there is provided a compound of Formula (VIc)

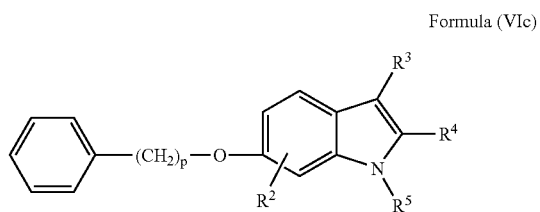

Formula (VIc)

wherein: p, q, $R^1$, $R^2$, $R^3$, $R^4$, and $R^5$ are as defined for Formula (VI) above with the proviso that (i) when $R^3$ is cyano then $R^4$ cannot be a group of Formula (II);

(ii) when $(R^1)_q$ is 4-methoxy or 3,4,5-trimethoxy, p is 1, $R^2$ is 5-methoxy, $R^3$ is hydrogen, cyanomethyl or 2-aminoethyl, $R^4$ is ethoxycarbonyl then $R^5$ cannot be hydrogen; and (iii) when q is 0, p is 1, $R^2$ is hydrogen or 5-methoxy, $R^3$ is methyl, cyanomethyl, 2-aminoethyl, 2-aminopropyl or hydroxyethyl, $R^4$ is hydrogen then $R^5$ cannot be hydrogen.

or a salt, pro-drug or solvate thereof;

According to a further aspect of the third feature of the invention there is provided a compound of Formula (VId)

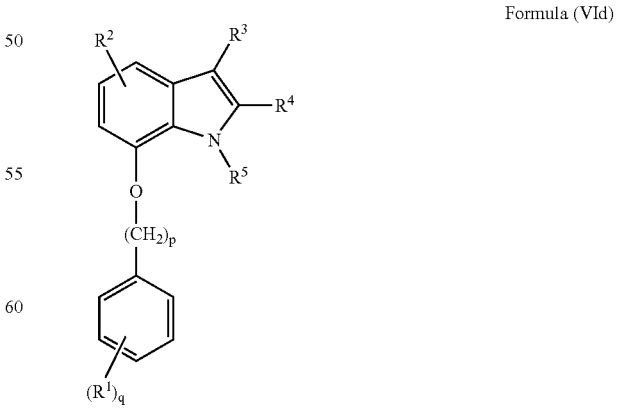

Formula (VId)

wherein: p, q, $R^1$, $R^2$, $R^3$, $R^4$, and $R^5$ are as defined for Formula (VI) above with the proviso that
(i) when $R^3$ is cyano then $R^4$ cannot be a group of Formula (II); and
(ii) when q is 0 or $(R^1)_q$ is 4-methoxy or 4-amino, p is 0 or 1 $R^3$ is hydrogen or methyl, $R^4$ is hydrogen or ethoxycarbonyl, then $R^5$ cannot be hydrogen or methyl.

or a salt, pro-drug or solvate thereof.

According to a further aspect of the third feature of the invention there is provided a compound of Formula (VIe)

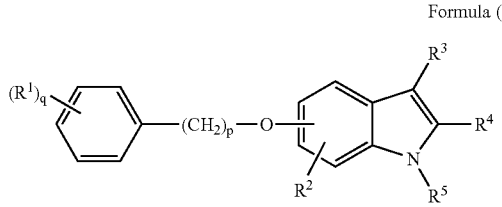

Formula (VIe)

wherein:
$R^1$ is independently selected from hydroxy, amino, alkanoylamino, —OPO$_3$H$_2$, or C$_{1-4}$alkoxy, wherein the amino group is optionally substituted by an amino acid residue and the hydroxy group is optionally esterified;
wherein: q is from 1 to 3, and p, $R^2$, $R^3$, $R^4$, and $R^5$ are as defined for Formula (VI) above with the proviso that
(i) when $R^3$ is cyano then $R^4$ cannot be a group of Formula (II); and
(ii) when $(R^1)_q$ is 4-methoxy, 4-amino or 3,4,5-trimethoxy, p is 0 or 1, $R^2$ is hydrogen or 5-methoxy, $R^3$ is hydrogen, cyanomethyl or 2-aminoethyl, $R^4$ is hydrogen or ethoxycarbonyl, then $R^5$ cannot be hydrogen or methyl;

or a salt, pro-drug or solvate thereof.

According to a further aspect of the third feature of the invention there is provided a pharmaceutical composition comprising a compound of Formula (VI), Formula (VIa), Formula (VIb), Formula (VIc), Formula (VId) or Formula (VIe) or pharmaceutically-acceptable salt, pro-drug or solvate thereof.

According to a further aspect of the third feature of the invention there is provided a pharmaceutical composition comprising a compound of Formula (VI), Formula (Via), Formula (VIb), Formula (VIc), Formula (VId) or Formula (VIe) or a pharmaceutically-acceptable salt, pro-drug or solvate thereof, in admixture with a pharmaceutically-acceptable diluent or carrier.

According to a further aspect of the third feature of the present invention there is provided the use of a compound of Formula (VI), Formula (VIa), Formula (VIb), Formula (VIc), Formula (VId) or Formula (VIe), or pharmaceutically-acceptable salt, pro-drug or solvate thereof for the manufacture of a medicament to inhibit and/or reverse and/or alleviate symptoms of angiogenesis and/or any disease state associated with angiogenesis.

According to a further aspect of the third feature of the invention there is provided a method of treatment, in a warm-blooded animal, to inhibit and/or reverse and/or alleviate symptoms of angiogenesis and/or any disease state associated with angiogenesis comprising administering to said warm-blooded animal a therapeutically (including prophylactically) effective amount of a compound of Formula (VI), Formula (Via), Formula (VIb), Formula (VIc), Formula (VId) or Formula (VIe), or a pharmaceutically acceptable salt, pro-drug or solvate thereof.

The invention also provides a further novel group of indole compounds. Thus, according to a fourth feature of the invention there is provided a compound of Formula (VII)

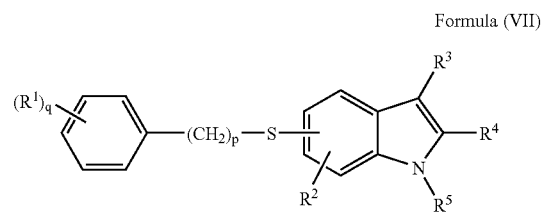

Formula (VII)

wherein:
$R^1$ is independently selected from halo, hydroxy, amino, alkanoylamino, —OPO$_3$H$_2$, or C$_{1-4}$alkoxy, wherein the amino group is optionally substituted by an amino acid residue and the hydroxy group is optionally esterified;
$R^2$ is selected from: hydrogen, C$_{1-4}$alkyl or C$_{1-4}$alkoxy;
$R^3$ and $R^4$ are independently selected from: hydrogen, C$_{1-4}$alkyl, C$_{1-4}$alkanoyl, C$_{1-4}$alkoxycarbonyl, C$_{1-4}$alkoxycarbonylC$_{1-4}$alkyl, C$_{1-4}$alkoxycarbonylamino, amino, aminoC$_{1-4}$alkyl, carbamoyl, carbamoylC$_{1-4}$alkyl, cyano, cyanoC$_{1-4}$alkyl, hydroxy, hydroxyC$_{1-4}$alkyl; or a group of Formula (II):

Formula (II)

$R^6$ is hydrogen or C$_{1-4}$alkyl;
$R^5$ and $R^7$ are independently selected from hydrogen, C$_{1-4}$alkyl or a group of Formula (III):

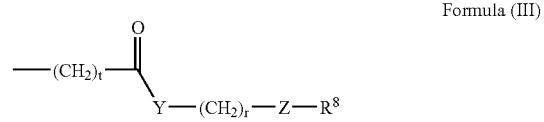

Formula (III)

wherein Y is selected from —NH—, —O— or a bond;
Z is selected from —NH—, —O—, —C(O)— or a bond;
r is an integer from 0 to 4;
t is an integer from 0 to 1;
$R^8$ is hydrogen, C$_{1-4}$alkyl, C$_{1-4}$alkoxy, aryl, 5 or 6 membered heterocyclyl, 5- or 6-membered heteroaryl, wherein aryl, heteroaryl or heterocyclyl is optionally substituted by C$_{1-4}$alkyl or C$_{1-4}$alkoxy, or a group of Formula (IV):

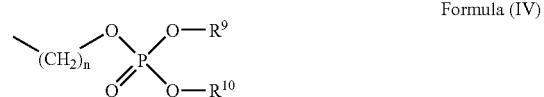

Formula (IV)

wherein n is an integer of from 1 to 6, and;
$R^9$ and $R^{10}$ are independently selected from hydrogen or C$_{1-4}$alkyl or aryl; and p is an integer from 0 to 1; and q is an integer from 0 to 3;

with the proviso that (i) when $R^3$ is cyano then $R^4$ cannot be a amino or a group of Formula (II);

(ii) when q is 0 or $(R^1)_q$ is 4-amino, p is 0 or 1, $R^2$ is hydrogen, $R^3$ is hydrogen, $R^4$ is hydrogen or ethoxycarbonyl, then $R^5$ cannot be hydrogen;

(iii) when q is 0, p is 0 or 1, $R^2$ is hydrogen, $R^3$ is hydrogen, methyl, cyano, 2-aminoethyl, 1-methyl-2-aminoethyl or 2-aminopropyl, $R^4$ is hydrogen or amino, then $R^5$ cannot be hydrogen; and (iv) when q is 0, p is 0, $R^2$ is hydrogen, $R^4$ is ethoxycarbonyl, then $R^5$ cannot be hydrogen;

or a salt, pro-drug or solvate thereof.

According to a further aspect of the fourth feature of the invention there is provided a compound of Formula (VIIa)

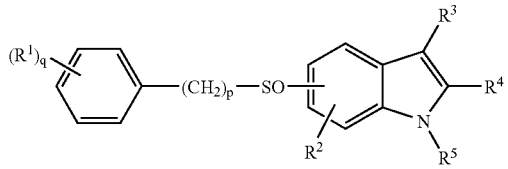

Formula (VIIa)

wherein:

wherein: p, q, $R^1$, $R^2$, $R^3$, $R^4$, and $R^5$ are as defined for Formula (VII) above with the proviso that (i) when $R^3$ is cyano then $R^4$ cannot be a group of Formula (II);

or a salt, pro-drug or solvate thereof.

According to a further aspect of the fourth feature of the invention there is provided a compound of Formula (VIIb)

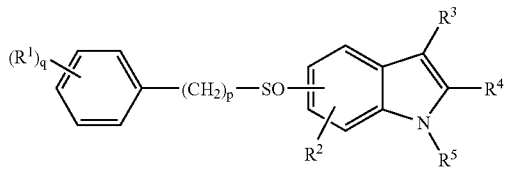

Formula (VIIb)

wherein:

wherein: p, q, $R^1$, $R^2$, $R^3$, $R^4$, and $R^5$ are as defined for Formula (VII) above with the proviso that (i) when $R^3$ is cyano then $R^4$ cannot be a group of Formula (II); and (ii) when $(R^1)_q$ is 4-chloro, p is 0, $R^2$ is hydrogen, $R^3$ is hydrogen, $R^4$ is hydrogen or ethoxycarbonyl, then $R^5$ cannot be hydrogen;

or a salt, pro-drug or solvate thereof.

According to a further aspect of the fourth feature of the invention there is provided a compound of Formula (VIIc)

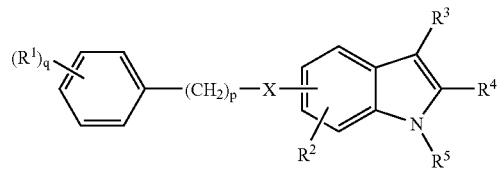

Formula (VIIc)

wherein:

X is selected from: —S—, —SO— or —SO$_2$—;

$R^1$ is independently selected from hydroxy, amino, alkanoylamino, —OPO$_3$H$_2$, or C$_{1-4}$alkoxy, wherein the amino group is optionally substituted by an amino acid residue and the hydroxy group is optionally esterified;

q is an integer from 0 to 3, preferably from 1 to 3;

and wherein: p, $R^2$, $R^3$, $R^4$, and $R^5$ are as defined for Formula (VI) above with the proviso that (i) when $R^3$ is cyano then $R^4$ cannot be a group of Formula (II);

(ii) when q is 0 or $(R^1)_q$ is 4-amino, p is 0 or 1, $R^2$ is hydrogen, $R^3$ is hydrogen, $R^4$ is hydrogen or ethoxycarbonyl, then $R^5$ cannot be hydrogen;

(iii) when q is 0, p is 0 or 1, $R^2$ is hydrogen, $R^3$ is hydrogen, methyl, cyano, 2-aminoethyl, 1-methyl-2-aminoethyl or 2-aminopropyl, $R^4$ is hydrogen or amino, then $R^5$ cannot be hydrogen; and (iv) when q is 0, p is 0, $R^2$ is hydrogen, $R^4$ is ethoxycarbonyl, then $R^5$ cannot be hydrogen;

or a salt, pro-drug or solvate thereof.

According to a further aspect of the fourth feature of the invention there is provided a compound of Formula (VIIe)

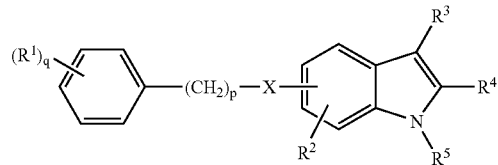

Formula (VIIe)

wherein:

X is selected from: —S—, —SO— or —SO$_2$—;

$R^1$ is independently selected from hydroxy, amino, alkanoylamino, —OPO$_3$H$_2$, or C$_{1-4}$alkoxy, wherein the amino group is optionally substituted by an amino acid residue and the hydroxy group is optionally esterified;

q is an integer from 1 to 3;

and wherein: p, $R^2$, $R^3$, $R^4$, and $R^5$ are as defined for Formula (VI) above with the proviso that (i) when $R^3$ is cyano then $R^4$ cannot be a group of Formula (II); and (ii) when $(R^1)_q$ is 4-amino, p is 0, $R^2$ is hydrogen, $R^3$ is hydrogen, $R^4$ is hydrogen or ethoxycarbonyl, then $R^5$ cannot be hydrogen;

or a salt, pro-drug or solvate thereof.

According to a further aspect of the fourth feature of the invention there is provided a pharmaceutical composition comprising a compound of Formula (VII), Formula (VIIa), Formula (VIb), Formula (VIc) or Formula (VIIe), or pharmaceutically-acceptable salt, or pro-drug solvate thereof.

According to a further aspect of the fourth feature of the invention there is provided a pharmaceutical composition comprising a compound of Formula (VII), Formula (VIIa) Formula (VIIb), Formula (VIIc) or Formula (VIIe), or a pharmaceutically-acceptable salt, pro-drug or solvate thereof, in admixture with a pharmaceutically-acceptable diluent or carrier.

According to a further aspect of the fourth feature of the present invention there is provided the use of a compound of Formula (VII), Formula (VIIa), Formula (VIIb), Formula (VIIc) or Formula (VIIe), or pharmaceutically acceptable salt, pro-drug or solvate thereof, for the manufacture of a medicament to inhibit and/or reverse and/or alleviate symptoms of angiogenesis and/or any disease state associated with angiogenesis.

According to a further aspect of the fourth feature of the invention there is provided a method of treatment, in a warm-blooded animal, to inhibit and/or reverse and/or alleviate symptoms of angiogenesis and/or any disease state associated with angiogenesis comprising administering to said warm-blooded animal a therapeutically (including prophylactically) effective amount of a compound of Formula (VII), Formula (VIIa), Formula (VIIb), Formula (VIIc) or Formula (VIIe), or a pharmaceutically acceptable salt, pro-drug or solvate thereof.

The invention also provides a further novel group of indole compounds. Thus, according to a fifth feature of the invention there is provided a compound of Formula (VIId)

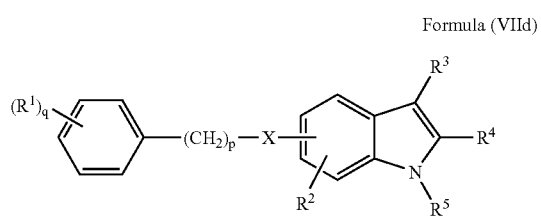

Formula (VIId)

wherein:

$R^1$ is independently selected from hydroxy, amino, alkanoylamino, —OPO$_3$H$_2$, or C$_{1-4}$alkoxy, wherein the amino group is optionally substituted by an amino acid residue and the hydroxy group is optionally esterified;

X is selected from: —O—, —S—, —SO— or —SO$_2$—;

$R^2$ is selected from: hydrogen, C$_{1-4}$alkyl or C$_{1-4}$alkoxy;

$R^3$ and $R^4$ are independently selected from: hydrogen, C$_{1-4}$alkyl, C$_{1-4}$alkanoyl, C$_{1-4}$alkoxycarbonyl, C$_{1-4}$alkoxycarbonylC$_{1-4}$alkyl, C$_{4-1}$ alkoxycarbonylamino, amino, aminoC$_{1-4}$alkyl, carbamoyl, carbamoylC$_{1-4}$alkyl, cyano, cyanoC$_{1-4}$alkyl, hydroxy, hydroxyC$_{1-4}$alkyl; or a group of Formula (II):

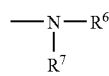

Formula (II)

$R^6$ is hydrogen or C$_{1-4}$alkyl;

$R^5$ and $R^7$ are independently selected from hydrogen, C$_{1-4}$alkyl or a group of Formula (III):

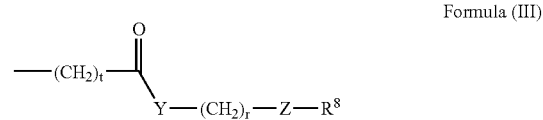

Formula (III)

wherein Y is selected from —NH—, —O— or a bond;
Z is selected from —NH—, —O—, —C(O)— or a bond;
r is an integer from 0 to 4;
t is an integer from 0 to 1;
$R^8$ is hydrogen, C$_{1-4}$alkyl, C$_{1-4}$alkoxy, aryl, 5 or 6 membered heterocyclyl, 5- or 6-membered heteroaryl, wherein aryl, heteroaryl or heterocyclyl is optionally substituted by C$_{1-4}$alkyl or C$_{1-4}$alkoxy, or a group of Formula (IV):

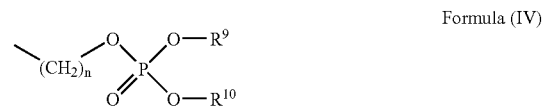

Formula (IV)

wherein n is an integer of from 1 to 6, and;
$R^9$ and $R^{10}$ are independently selected from hydrogen or C$_{1-4}$alkyl or aryl; and
p is an integer from 0 to 1; and
q is an integer from 1 to 3;

with the proviso that
(i) when $R^3$ is cyano then $R^4$ cannot be a group of Formula (II); and
(ii) when $(R^1)_q$ is 4-methoxy, 4-amino, 4-chloro or 3,4,5-trimethoxy, p is 0 or 1, $R^2$ is hydrogen or 5-methoxy, $R^3$ is hydrogen, cyanomethyl or 2-aminoethyl, $R^4$ is hydrogen or ethoxycarbonyl, then $R^5$ cannot be hydrogen or methyl;

or a salt, pro-drug or solvate thereof.

According to a further aspect of the fifth feature of the invention there is provided a pharmaceutical composition comprising a compound of Formula (VIId), or pharmaceutically-acceptable salt, or pro-drug solvate thereof.

According to a further aspect of the fifth feature of the invention there is provided a pharmaceutical composition comprising a compound of Formula (VIId), or a pharmaceutically-acceptable salt, pro-drug or solvate thereof, in admixture with a pharmaceutically-acceptable diluent or carrier.

According to a further aspect of the fifth feature of the present invention there is provided the use of a compound of Formula (VIId), or pharmaceutically acceptable salt, pro-drug or solvate thereof, for the manufacture of a medicament to inhibit and/or reverse and/or alleviate symptoms of angiogenesis and/or any disease state associated with angiogenesis.

According to a further aspect of the fifth feature of the invention there is provided a method of treatment, in a warm-blooded animal, to inhibit and/or reverse and/or alleviate symptoms of angiogenesis and/or any disease state associated with angiogenesis comprising administering to said warm-blooded animal a therapeutically (including prophylactically) effective amount of a compound of Formula (VIId), or a pharmaceutically acceptable salt, pro-drug or solvate thereof.

Whilst pharmaceutically acceptable salts of compounds of the invention are preferred, other non-pharmaceutically acceptable salts of compounds of the invention may also be useful, for example in the preparation of pharmaceutically-acceptable salts of compounds of the invention.

For the avoidance of doubt when q is 0, all positions on the phenyl ring are substituted by hydrogen.

For the avoidance of doubt the use of the term $(R_1)_q$ when q is from 1 to 3, means that there are 1, 2 or 3 $R^1$ substituents on the phenyl ring, which when q is 2 or 3 can be the same group or different groups. For example, where $(R_1)_q$ is 3-chloro-4-methoxy then q is 2 and the phenyl ring has a chloro group at the 3-position and a methoxy group at the 4-position, in relation to the —$(CH_2)_pX$— group, and for example, when $(R_1)_q$ is di-halo, then q is 2 and the phenyl ring has two halo substituents which may be the same group or different groups, wherein the halo groups occupy 2 positions on the phenyl ring.

For the avoidance of doubt the use of the term $(R_1)_{q-1}$ means there is one substituent on the phenyl ring as indicated in the respective formula and the phenyl ring can either bear no further substituents or may bear one or two further substituents. Where there are two further substituents these may the same group or different groups.

In this specification the generic term 'alkyl' includes both straight-chain and branched-chain alkyl groups. However references to individual alkyl groups such as 'propyl' are specific for the straight-chain version only and references to individual branched-chain alkyl groups such as 'isopropyl' are specific for the branched-chain version only. An analogous convention applies to other generic terms.

The term "aryl" refers to phenyl or naphthyl.

The term "heteroaryl" refers to a 5–10 membered aromatic mono or bicyclic ring containing up to 5 heteroatoms independently selected from nitrogen, oxygen or sulphur, linked via ring carbon atoms or ring nitrogen atoms where a bond from a nitrogen is allowed, for example no bond is possible to the nitrogen of a pyridine ring, but a bond is possible through the 1-nitrogen of a pyrazole ring. Examples of 5- or 6-membered heteroaryl ring systems include pyrrole, furan, imidazole, triazole, pyrazine, pyrimidine, pyridazine, pyridine, isoxazole, oxazole, 1,2,4 oxadiazole, isothiazole, thiazole and thiophene. A 9 or 10 membered bicyclic heteroaryl ring system is an aromatic bicyclic ring system comprising a 6-membered ring fused to either a 5 membered ring or another 6 membered ring. Examples of 5/6 and 6/6 bicyclic ring systems include benzofuran, benzimidazole, benzthiophene, benzthiazole, benzisothiazole, benzoxazole, benzisoxazole, indole, pyridoimidazole, pyrimidoimidazole, quinoline, isoquinoline, quinoxaline, quinazoline, phthalazine, cinnoline and naphthyridine.

The term "heterocyclyl" refers to a 5–10 membered saturated or partially saturated mono or bicyclic ring containing up to 5 heteroatoms selected from nitrogen, oxygen or sulphur linked via ring carbon atoms or ring nitrogen atoms. Examples of 'heterocyclyl' include pyrrolinyl, pyrrolidinyl, morpholinyl, piperidinyl, piperazinyl, dihydropyridinyl and dihydropyrimidinyl The term halo refers to fluoro, chloro, bromo or iodo.

The term "carbamoyl" refers to the group —C(O)—$NH_2$.

The term amino acid residue is defined as that derived from the coupling of an L-amino acid with an amino group via an amide bond. This bond can either be formed via a carboxylate group on the amino acid backbone or via a side chain carboxylate group, preferably via a carboxylate group on the amino acid backbone. Amino acid residues include those derived from natural and non-natural amino acids, preferably natural amino acids and include α-amino acids β-amino acids and γ-amino acids. For the avoidance of doubt amino acids include those with the generic structure:

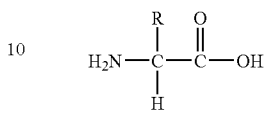

where R is the amino acid side chain: The definition of amino acid also includes amino acid analogues which have additional methylene groups within the amino acid backbone, for example β-alanine and amino acids which are not naturally occurring such as cyclohexylalanine. Preferably an animo acid residue is a naturally-occurring amino acid residue.

Preferred amino acids include glycine, alanine, valine, leucine, isoleucine, methionine, proline, phenylalanine, tryptophan, serine, threonine, cysteine, tyrosine, asparagine, glutamine, aspartic acid, glutamic acid, lysine, arginine, histidine, β-alanine and ornithine. More preferred amino acids include glutamic acid, serine, threonine, arginine, glycine, alanine, β-alanine and lysine. Especially preferred amino acids include glutamic acid, serine, and glycine.

Esterifying groups at $R^1$ are esterifying groups which increase the solubility of the molecule in water at a pH of approximately pH=7. Such groups include groups with ionisable groups, such as acidic functions or basic functions and groups containing a hydrophilic function. Basic functions include: amino, morpholino, piperidino, piperazino, pyrrolidino, amino acids and imidazolino. Acidic functions include: carboxy, sulphonic acid, phosphate, sulphate and acid mimetics such as tetrazolyl. Hydrophilic groups include hydroxyl.

Suitable $R^1$ groups wherein hydroxy is esterfied include: $C_{1-6}$alkanoyloxy, arylcarbonyloxy, heterocyclylcarbonyloxy, heteroarylcarbonyloxy wherein the $R^1$ group is optionally substituted with from 1 to 3 groups selected from $C_{1-4}$alkyl, $C_{1-4}$alkanoyl, $C_{1-4}$alkanoyl$C_{1-4}$alkyl, $C_{1-4}$alkanoylheterocyclyl, hydroxy, hydroxy$C_{1-4}$alkyl, carboxy, carboxyphenyl, phosphono, phosphono$C_{1-4}$alkyl, amino, amino$C_{1-4}$alkyl, N—$C_{1-4}$alkylamino, N,N-di$C_{1-4}$alkylamino, carbamoyl, carbamoyl$C_{1-4}$alkyl, heterocyclyl, heterocyclyl$C_{1-4}$alkyl, heterocyclylcarbonyl, heterocyclyl$C_{1-4}$alkanoylamino, carbamoylheterocyclyl, [wherein optional substituents comprising heterocyclyl are optionally further substituted by $C_{1-4}$alkyl, hydroxy$C_{1-4}$alkyl, $C_{1-4}$alkoxy$C_{1-4}$alkyl, $C_{1-4}$alkanoyl and formyl, wherein the carbamoyl and amino optional substituents are optionally further N-substituted by $C_{1-4}$alkyl, di-$C_{1-4}$alkyl, hydroxy$C_{1-4}$alkyl, di-(hydroxy$C_{1-4}$alkyl), carboxy$C_{1-4}$alkyl, and wherein the amino group is optionally substituted by an amino acid residue] with the proviso that when $R_1$ is $C_{1-6}$alkanoyloxy or arylcarbonyloxy $R_1$ is not unsubstituted and $R_1$ is not substituted by $C_{1-4}$alkyl.

More preferred $R^1$ groups wherein hydroxy is esterfied include: carboxypentanoyloxy, 4-carboxyphenylpropanoyloxy; 4-(N-methylpipeaizin-1-ylethyl)phenylcarbonyloxy, 4-(piperazin-1-ylethyl)phenylcarbonyloxy, 4-[N-di-(hydroxyethyl)aminomethyl]phenylcarbonyloxy, 3-(N-acetylpiperazin-1-ylethyl)phenylcarbonyloxy, 3-[N-di-(hydroxyethyl)aminomethyl]phenylcarbonyloxy, 4-(N- methylpiperazin-1-ylpropanoylamino)phenylcarbonyloxy, N-methylpiperazin-1-ylcarbonylpropanoyloxy, N-di-(hydroxyethyl)aminocarbonylpropanoyloxy, piperazin-1-ylcarbonylpropanoyloxy, (N-acetylpiperazin-1-yl)carbonylpropanoyloxy, (N-di-(hydroxyethyl) aminocarbonylpropanoyloxy, and 4-(piperazin-1-ylmethyl)phenylcarbonyloxy.

Further preferred $R^1$ groups wherein hydroxy is esterfied include: 4-(N-methylpiperazin-1-ylpropanoylamino)phenylcarbonyloxy, N-methylpiperazin-1-ylcarbonylpropanoyloxy and N-di-(hydroxyethyl)aminocarbonylpropanoyloxy.

Examples of $C_{1-4}$alkyl include methyl, ethyl, propyl, isopropyl, sec-butyl and tert-butyl; examples of $C_{1-4}$alkoxy include methoxy, ethoxy, propoxy and tert-butoxy; examples of $C_{1-4}$alkanoyl include acetyl, propanoyl and butanoyl; examples of $C_{1-4}$alkanoylamino include acetylamino, propanoylamino and butanoylamino; examples of $C_{1-4}$alkoxycarbonyl include methoxycarbonyl, ethoxycarbonyl and tert-butyloxycarbonyl; examples of $C_{1-4}$alkoxycarbonyl$C_{1-4}$alkyl include methoxycarbonylethyl, ethoxycarbonylmethyl and tert-butyloxycarbonylbutyl; examples of $C_{1-4}$alkoxycarbonylamino include methoxycarbonylamino, ethoxycarbonylamino and tert-butyloxycarbonylamino; examples of amino$C_{1-4}$alkyl include aminomethyl, aminoethyl and aminopropyl; examples of cyano$C_{1-4}$alkyl include cyanomethyl, cyanoethyl and cyanopropyl; examples of carbamoyl$C_{1-4}$alkyl include carbamoylmethyl, carbamoylethyl and carbamoylpropyl; examples of hydroxy$C_{1-4}$alkyl include hydroxymethyl, hydroxyethyl and hydroxypropyl.

It is to be understood that, insofar as certain of the compounds in the different features of the invention may exist in optically active or racemic forms by virtue of one or more asymmetric carbon atoms, the invention includes in its definition any such optically active or racemic form which possesses the property of inhibiting and/or reversing and/or alleviating the symptoms of angiogenesis and/or any disease states associated with angiogenesis. The synthesis of optically active forms may be carried out by standard techniques of organic chemistry well known in the art, for example by synthesis from optically active starting materials or by resolution of a racemic form. Similarly, activity of these compounds may be evaluated using the standard laboratory techniques referred to hereinafter.

The invention also relates to any and all tautomeric forms of the compounds of the different features of the invention that possess the property of inhibiting and/or reversing and/or alleviating the symptoms of angiogenesis and/or any disease states associated with angiogenesis.

It will also be understood that certain compounds of the present invention may exist in solvated, for example hydrated, as well as unsolvated forms. It is to be understood that the present invention encompasses all such solvated forms which possess the property of inhibiting and/or reversing and/or alleviating the symptoms of angiogenesis and/or any disease states associated with angiogenesis.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a carbazole derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically acceptable cation, for example a salt with methylamine, dimethylamine, trimethylamine, piperidine, morpholine or tris-(2-hydroxyethyl)amine.

A preferred group of values of $R^1$ in each feature of the invention is hydroxy, amino, —$OPO_3H_2$, or $C_{1-4}$alkoxy, wherein the amino group is optionally substituted by an amino acid residue and the hydroxy group is optionally esterified. A further preferred group of values of $R^1$ in each feature of the invention is hydroxy, amino, —$OPO_3H_2$, or $C_{1-4}$alkoxy, wherein the amino group is optionally substituted by an amino acid residue. A more further preferred group of values of $R^1$ in each feature of the invention is hydroxy, amino, —$OPO_3H_2$, methoxy, ethoxy, glutamylamino preferably α-glutamylamino, serylamino, glycylamino or alanylamino. A yet more further preferred group of values of $R^1$ in each feature of the invention is hydroxy, α-glutamylamino, seryl, —$OPO_3H_2$ or methoxy. A most preferred group of values of $R^1$ in each feature of the invention is 3,4-dimethoxy, 3,5-dimethoxy, 2,5-dimethoxy, 3,4,5-trimethoxy, 4-hydroxy-3,5-dimethoxy or 4-phosphonooxy-3,5-dimethoxy.

A preferred group of values in each feature of the invention for p is 0 or 1. More preferably in each features of the invention p is 0.

A preferred group of values in each feature of the invention for q is 2 or 3. More preferably in each features of the invention q is 3.

A preferred group of values of X in the first and second features of the invention is —O—, —S— or —$SO_2$—. Most preferably X is —S—.

A preferred group of values for $R^2$ in each feature of the invention is hydrogen.

A preferred group of values for $R^3$ in each feature of the invention is hydrogen, $C_{1-4}$alkanoyl, $C_{1-4}$alkoxycarbonyl, hydroxy$C_{1-4}$alkyl, carbamoyl or $C_{1-4}$alkylcarbamoyl, A more preferred group of values for $R^3$ in each feature of the invention is cyano, $C_{1-4}$alkylcyano, carbamoyl or $C_{1-4}$alkylcarbamoyl. A most preferred group of values for $R^3$ in each feature of the invention is $C_{1-4}$alkylcyano or cyano.

A preferred group of values for $R^4$ in each feature of the invention is hydrogen, carbamoyl, carbamoyl$C_{1-4}$alkyl, $C_{1-4}$alkoxy, $C_{1-4}$alkoxycarbonyl, cyano or a group of Formula (II). A more preferred group of values for $R^4$ is hydrogen, cyano, carbamoyl, carbamoyl$C_{1-4}$alkyl, $C_{1-4}$alkoxy or $C_{1-4}$alkoxycarbonyl. A most preferred value for $R^4$ is hydrogen.

A preferred group of values for $R^5$ in each aspect of the invention is hydrogen, $C_{1-4}$alkyl or a group of Formula (III) wherein t, Y, r, Z and $R^8$ are as defined above. A more preferred group of values for $R^5$ in each aspect of the invention is hydrogen or $C_{1-4}$alkyl. A further preferred value for $R^5$ is hydrogen, methyl or ethyl. A most preferred value for $R^5$ is methyl.

A preferred group of values for $R^6$ in each aspect of the invention is hydrogen or $C_{1-4}$alkyl. More preferably $R^6$ is hydrogen or methyl. Most preferably $R^6$ is hydrogen.

A preferred group of values for $R^7$ in each aspect of the invention is hydrogen, methyl, or a group of Formula (III). A most preferred group of values for $R^7$ is hydrogen or a group of Formula (III). A most preferred value of $R^7$ is hydrogen.

A preferred group of values for t in each aspect of the invention is 0 or 1. A most preferred value for t in each aspect of the invention is 0.

A preferred group of values for Y in each aspect of the invention is or a bond. A most preferred group of values for Y in each aspect of the invention is —O—.

A preferred group of values for r in each aspect of the invention is 1, 2 or 3. A most preferred values for r in each aspect of the invention is 1.

A preferred group of values for Z in each aspect of the invention is —C(O)— or a bond. A most preferred group of values for Z in each aspect of the invention is a bond.

A preferred group of values for $R^8$ in each aspect of the invention is hydrogen, $C_4$alkyl $C_{1-4}$alkoxy, an aryl group, a 6-membered heterocyclic group or a group of Formula (IV), wherein the aryl group and heterocyclic group are optionally substituted by $C_{1-4}$alkyl or $C_{1-4}$alkoxy: More preferably $R^8$ is a non-aromatic heterocyclic group, an aryl group or a group of Formula (IV), wherein the aryl group and non-aromatic heterocyclic group are optionally substituted by $C_{1-4}$alkyl or $C_{1-4}$alkoxy. Further preferably $R^8$ is phenyl, morpholino, piperazinyl or a group of Formula (IV), wherein the phenyl, morpholino and piperazinyl group are optionally substituted by methyl or acetyl and $R^9$ and $R^{10}$ are both hydrogen. Most preferably $R^8$ is phenyl, morpholino or 4-methyl-piperazin-1-yl.

A preferred group of values for n in each aspect of the invention is 2 or 3. Preferably n is 2.

A preferred group of values for $R^9$ and $R^{10}$ in each aspect of the invention is $R^9$ and $R^{10}$ are independently selected from hydrogen or an alkaryl group, preferably —$(CH_2)_m$— Ph where m is an integer of from 1 to 6, preferably m is 1. More preferably $R^9$ and $R^{10}$ are independently selected from hydrogen or benzyl (—$CH_2$—Ph). Preferably $R^9$ and $R^{10}$ are both hydrogen.

A preferred group of values for a group of Formula (III) is phenoxycarbonyl, phosphonooxyethylaminocarbonyl, 4-methylpiperazin-1-ylpropoxycarbonyl, carbamoylmethyl, 4-acetyl-piperazin-1-ylethoxycarbonyl, 4-methyl-piperazin-1-ylcarbonylpropanoyl and morpholinoethoxycarbonyl. Preferably phenoxycarbonyl, 4-methylpiperazin-1-ylpropoxycarbonyl or carbamoylmethyl.

Preferably only one of $R^5$ and $R^7$ is a group of Formula (III).

In the following preferred groups of compounds of each aspect of the invention values for $R^1$, $R^2$, $R^3$, $R^4$, $R^5$, $R^6$, $R^7$, $R^8$, $R^9$, $R^{10}$, n, p, q, r, t, X, Y and Z are as hereinbefore defined, unless specifically defined with a preferred group of compounds.

A preferred group of compounds in the first and second features of the invention; comprise compounds wherein:
X is —O—;

or salt, pro-drug or solvate thereof.

A preferred group of compounds in the first and second features of the invention; comprise compounds wherein:
X is —S—, —SO— or —$S(O)_2$—;

or salt, pro-drug or solvate thereof.

A further preferred group of compounds in each feature of the invention, comprise compounds wherein:
$R^3$ is selected from cyano or cyano$C_{1-4}$alkyl, preferably cyano;

or salt, pro-drug or solvate thereof.

A further preferred group of compounds of each feature of the invention; comprise compounds wherein:
$R^1$ is amino, hydroxy or —$OPO_3H_2$, wherein the amino group is optionally substituted by an amino acid residue and the hydroxy group is optionally esterified;

or salt, pro-drug or solvate thereof.

A further preferred group of compounds of each feature of the invention; comprise compounds wherein:

$R^1$ is independently selected from hydroxy, amino, —$OPO_3H_2$, or $C_{1-4}$alkoxy, wherein the amino group is optionally substituted by an amino acid residue and the hydroxy group is optionally esterified;
$R^3$ is selected from carbamoyl, carbamoyl$C_{1-4}$alkyl, cyano or cyano$C_{1-4}$alkyl; preferably cyano or cyano$C_{1-4}$alkyl; and
$R^5$ is hydrogen or $C_{1-4}$alkyl;

or salt, pro-drug or solvate thereof.

A further preferred group of compounds of the first and second features of the invention, comprise compounds wherein:
$R^1$ is independently selected from hydroxy, amino, —$OPO_3H_2$, or $C_{1-4}$alkoxy, wherein the amino group is optionally substituted by an amino acid residue and the hydroxy group is optionally esterified;
X is —S— or —O—;
$R^3$ is selected from carbamoyl, carbamoyl$C_{1-4}$alkyl, cyano or cyano$C_{1-4}$alkyl; preferably cyano or cyano$C_{1-4}$alkyl; and
$R^5$ is hydrogen or $C_{1-4}$alkyl;

or salt, pro-drug or solvate thereof.

A further preferred group of compounds in each feature of the invention, comprise compounds wherein:
$R^1$ is independently selected from hydroxy, —$OPO_3H_2$, or $C_{1-4}$alkoxy;
$R^3$ is selected from carbamoyl, carbamoyl$C_{1-4}$alkyl, cyano or cyano$C_{1-4}$alkyl; preferably cyano or cyano$C_{1-4}$alkyl; and
$R^5$ is hydrogen or $C_{1-4}$alkyl;

or salt, pro-drug or solvate thereof.

A further preferred group of compounds of the first and second features of the invention, comprise compounds wherein:
$R^1$ is independently selected from hydroxy, —$OPO_3H_2$, or $C_{1-4}$alkoxy;
X is —S— or —O—;
$R^3$ is selected from carbamoyl, carbamoyl$C_{1-4}$alkyl, cyano or cyano$C_{1-4}$alkyl; preferably cyano or cyano$C_{1-4}$alkyl; and
$R^5$ is hydrogen or $C_{1-4}$alkyl;

or salt, pro-drug or solvate thereof.

A further preferred group of compounds in each feature of the invention, comprise compounds wherein:
$R^1$ is selected from hydroxy-dimethoxy, trimethoxy or phosphonooxy-dimethoxy; preferably 3,4-dimethoxy, 3,5-dimethoxy, 2,5-dimethoxy, 3,4,5-trimethoxy, 4-hydroxy-3,5-dimethoxy or 4-phosphonooxy-3,5-dimethoxy;
$R^3$ is selected from carbamoyl, carbamoyl$C_{1-4}$alkyl, cyano or cyano$C_{1-4}$alkyl; preferably cyano or cyano$C_{1-4}$alkyl; and
$R^5$ is hydrogen or $C_{1-4}$alkyl;

or salt, pro-drug or solvate thereof.

A further preferred group of compounds of the first and second features of the invention, comprise compounds wherein:
$R^1$ is selected from hydroxy-dimethoxy, trimethoxy or phosphonooxy-dimethoxy; preferably 3,4-dimethoxy, 3,5-dimethoxy, 2,5-dimethoxy, 3,4,5-trimethoxy, 4-hydroxy-3,5-dimethoxy or 4-phosphonooxy-3,5-dimethoxy;
X is —S— or —O—;
$R^3$ is selected from carbamoyl, carbamoyl$C_{1-4}$alkyl, cyano or cyano$C_{1-4}$alkyl; preferably cyano or cyano$C_{1-4}$alkyl; and $R^5$ is hydrogen or $C_{1-4}$alkyl;

or salt, pro-drug or solvate thereof.

A further preferred group of compounds of the first and second features of the invention comprise compounds, wherein:

$R^1$ is selected from hydroxy, amino, —OPO$_3$H$_2$, or $C_{1-4}$alkoxy, wherein the amino group is optionally substituted by an amino acid residue;

$R^2$ is hydrogen;

X is selected from: —O—, or —S—;

p is 0 or 1;

q is an integer from 1 to 3;

$R^3$ is selected from: hydrogen, cyano, carbamoyl, carbamoyl$C_{1-4}$alkyl, $C_{1-4}$alkanoy, $C_{1-4}$alkoxycarbonyl;

$R^4$ is selected from: hydrogen, cyano or carbamoyl;

$R^5$ is hydrogen or $C_{1-4}$alkyl or salt, pro-drug or solvate thereof.

Particular compounds of each feature of the invention include:

3-cyano-5-phenylsulphanyl-1H-indole;
3-cyano-5-phenoxy-1H-indole;
3-cyano-5-(4-hydroxyphenoxy)-1H-indole;
2-cyano-5-benzyloxy-1H-indole;
3-Carbamoyl-5-phenoxy-1H-indole; and
3-Carbamoyl-5-(4-hydroxyphenoxy)-1H-indole.

or salt, pro-drug or solvate thereof

More particular compounds of each feature of the invention include:

1-methyl-3-cyano-5-(4-hydroxy-3,5-dimethoxyphenoxy)-1H-indole;
1-methyl-3-cyano-5-(4-phosphonoxy-3,5-dimethoxyphenoxy)-1H-indole;
3-cyano-5-(3,4-dimethoxyphenylsulphanyl)-1H-indole;
1-methyl-3-cyano-5-(3,4-dimethoxyphenylsulphanyl)-1H-indole; and
1-Methyl-3-cyano-5-(4-hydroxy-3,5-dimethoxyphenoxy)-1H-indole.

or salt, pro-drug or solvate thereof

A compound of the invention or a pharmaceutically-acceptable salt, or solvate thereof, may be prepared by any process known to be applicable to the preparation of chemically related compounds. Such processes, when used to prepare a compound of the invention or a pharmaceutically-acceptable salt, or solvate thereof, are provided as a further feature of the invention and are illustrated by the following representative examples in which $R^1$, $R^2$, $R^3$, $R^4$, $R^5$, $R^6$, $R^7$, $R^8$, $R^9$, $R^{10}$, X, Y, Z, n, p, q, r and t have the same meaning as herein before defined. The reader is referred to Advanced Organic Chemistry, 4$^{th}$ Edition, by Jerry March, published by John Wiley & Sons 1992, for general guidance on reaction conditions and reagents. The reader is referred to Protective Groups in Organic Synthesis 2$^{nd}$ Edition, by Green et al, published by John Wiley & Sons for general guidance on protecting groups.

Thus, according to the sixth aspect of the invention there is provided a process for preparing a compound of Formula (I), or salt, solvate or pro-drug thereof, which process (wherein $R^1$, $R^2$, $R^3$, $R^4$, $R^5$, $R^6$, $R^7$, $R^8$, $R^9$, $R^{10}$, $R^{11}$, X, Y, Z, n, p, q, r and t are unless otherwise specified as defined in Formula (I)) comprising:

a) for compounds of Formula (I) wherein X is —O—, or —S—, reacting a compound of Formula (A) with a compound of Formula (B),

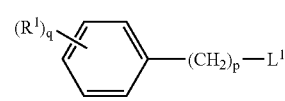
Formula (A)

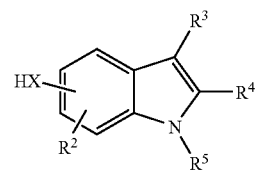
Formula (B)

wherein $L^1$ is a leaving group;

b) for compounds of Formula (I) in which $R^1$ comprises amino, reduction of a compound of Formula (C):

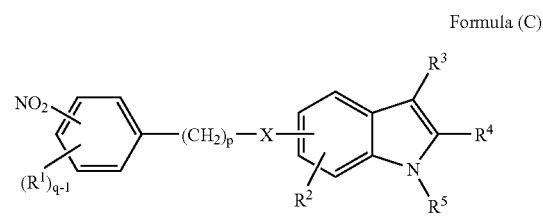
Formula (C)

c) for compounds of Formula (I) wherein $R^5$ is $C_{1-4}$alkyl, reacting a compound of Formula (I) wherein $R^5$ is hydrogen with a suitable alkylhalide, d) for compounds of Formula (I) wherein $R^1$ comprises an amino group substituted by an amino acid residue, reacting a compound of Formula (D) with an amino acid,

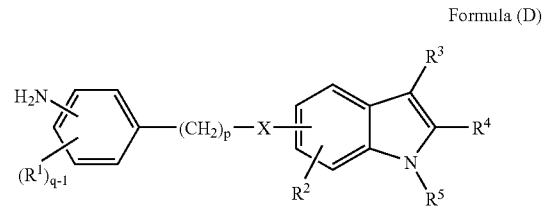
Formula (D)

e) for compounds of Formula (I) in which $R^3$ is a group of Formula (II) and $R^7$ is a group of Formula (III), reacting a compounds of Formula (I) in which $R^3$ is a group of Formula (II) and $R^7$ is hydrogen with compounds of Formula (E) below, in which $L^2$ is a leaving group:

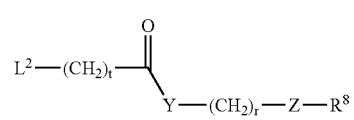
Formula (E)

f) for compounds of Formula (I) in which $R^4$ is hydrogen, reacting a compounds of Formula (I) in which $R^3$ is hydrogen and $R^4$ is hydrogen with a compounds of $L^3R^3$ in which $L^3$ is a leaving group;

g) for compounds of Formula (I) in which $R^1$ is an esterified hydroxyl group, reacting a compound of Formula (F) with an appropriate carboxylic acid or carboxylic acid derivative;

Formula (F)

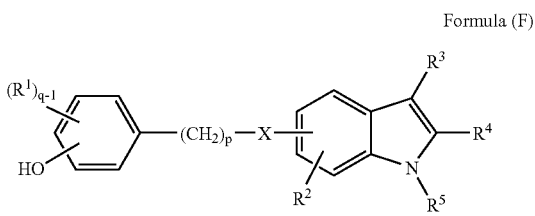

and thereafter if necessary:
i) converting a compound of Formula (I) into another compound of Formula (I);
ii) removing any protecting groups;
iii) forming a salt, pro-drug or solvate.

According to a further feature of the sixth aspect of the invention there is provided the processes a), b), c), d), e), f) and g) described above for the preparation of compounds of the Formula (I), or a salt, pro-drug or solvate thereof.

Specific reaction conditions for the above reactions are as follows:

Process a) Compounds of Formula (A) and compound of Formula (B) can be reacted together in an organic solvent, at a temperature between room temperature and about 80° C., optionally in the presence of a base such as sodium hydride, potassium carbonate or triethylamine.

Process b) The conditions for reduction of a compound of Formula (C) are well known in the art. Examples of reducing agents include hydrogen and a hydrogenation catalyst (for example palladium on carbon), iron and acetic acid, and zinc and hydrochloric acid. The reaction is preferably carried out in the presence of a suitable solvent such as an alcohol, for example methanol or ethanol, and at a temperature in the range of 0–80° C., preferably at or near room temperature. Further examples of reducing conditions include sodium dithionite in the presence of a base, preferably sodium bicarbonate in a suitable solvent such as DMF or N-methyl-pyrrolidone.

Compounds of Formula (C) can be prepared by reaction of a compound of Formual (F) and a compound of Formula (G) as described in process a).

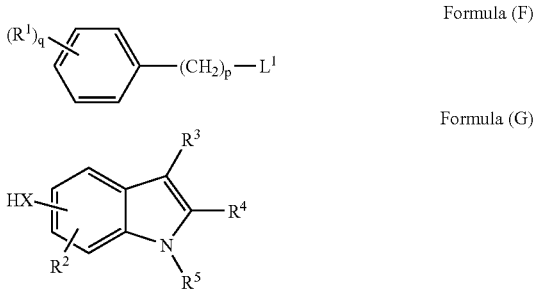

Formula (F)

Formula (G)

Process c) Compounds of Formula (I) wherein $R_2$ is hydrogen and a suitable alkyl halide may be reacted together in a suitable organic solvent such as DMF or DMSO, in the presence of a base, such as sodium hydride or potassium carbonate at a temperature between about room temperature and about 80° C.

Process d) Compound of Formula (D) can be reacted with an amino acid using a suitable amide bond forming reaction. Amide bond forming reactions are well known in the art, for example, a carbodiimide coupling reaction can be performed with EDAC in the presence of DMAP in a suitable solvent such as methylene chloride, chloroform or DMF at room temperature.

Process e) Compounds of Formula (I) in which $R^3$ is hydrogen can be reacted with compounds of Formula (E) under conditions well known in the art. For example $L^2$ may be chloro or p-nitrophenoxy. When $L^2$ is Chloro this is carried out in the presence of a base, preferably pyridine.

Process f) Compounds of Formula (I) in which $R^3$ is hydrogen and $R^4$ is hydrogen can be reacted with compounds of the formula $L^3R^3$ in acetonitrile or diethyl ether in the presence of a base such as triethylamine at a temperature between 0° C. and room temperature;

Process g) Processes for the formulation of an ester between a hydroxyl group and a carboxylic acid or carboxylic acid derivative are well know in the art. For example this reaction an acid chloride can be reacted with an alcohol in the presence of a base such as triethylemaine. A carboxylic acid derivative is any derivative of a carboxylic acid which when reacted with a hydroxyl under appropriate conditions will form an ester bond. Examples of carboxylic acid derivatives include an acid chloride.

The compounds used as starting points for the reactions described above are commercially available or they are known compounds or they are prepared by processes known in the art.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

In order to use a compound of the Formula (I), or a pharmaceutically-acceptable salt or in vivo cleavable ester thereof, for the therapeutic treatment (including prophylactic treatment) of mammals including humans, it is normally formulated in accordance with standard pharmaceutical practice as a pharmaceutical composition.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 µm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula (I) will naturally vary according to the nature and severity of the conditions, the age and sex of the animal or patient and the route of administration, according to well known principles of medicine.

In using a compound of the Formula (I) for therapeutic or prophylactic purposes it will generally be administered so that a daily dose in the range of, for example, 0.5 mg to 75 mg per kg body weight is received, given if required in divided doses. In general lower doses will be administered when a parenteral route is employed. Thus, for example, for intravenous administration, a dose in the range of, for example, 0.5 mg to 20 mg per kg body weight will generally be used. Intravenous administration is however preferred, typically, intravenous doses of about 10 mg to 500 mg per patient of a compound of this invention.

The vascular damaging treatment defined hereinbefore may be applied as a sole therapy or may involve, in addition to the compound of the invention, conventional surgery or radiotherapy or chemotherapy. Such chemotherapy may include one or more of the following categories of antitumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD 1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin $α_vβ3$ function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multidrug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

Examples of conditions wherein such combination therapy may be appropriate include: cancer, diabetes, psoriasis, rheumatoid arthritis, Kaposi's sarcoma, haemangioma, acute and chronic nephropathies, atheroma, arterial restenosis, autoimmune diseases, acute inflammation, endometriosis, dysfunctional uterine bleeding and ocular diseases with retinal vessel proliferation.

According to the seventh feature of the present invention there is provided a compound of Formula (I), or salt, solvate or thereof, preferably in the form of a pharmaceutical composition, which when dosed in divided doses (also known as split doses) produces a greater anti-tumour effect than when a single dose is given.

Anti-tumour effects include but are not limited to, inhibition of tumour growth, tumour growth delay, regression of tumour, shrinkage of tumour, increased time to re-growth of tumour on cessation of treatment, slowing of disease progression. It is expected that when a compound of the present invention is administered to a warm-blooded animal such as a human, in need of treatment for cancer involving a solid tumour, said method of treatment will produce an effect, as measured by, for example, one or more of: the extent of the anti-tumour effect, the response rate, the time to disease progression and the survival rate.

According to a further aspect of the seventh feature of the present invention there is provided a method for the production of a vascular damaging effect in a warm-blooded animal such as a human, which comprises administering to said animal in divided doses an effective amount of a compound of Formula (I), or salt, or solvate thereof, preferably in the form of a pharmaceutical composition.

According to a further aspect of the seventh feature of the present invention there is provided a method for the treatment of a cancer involving a solid tumour in a warm-blooded animal such as a human, which comprises administering to said animal in divided doses an effective amount of a compound of Formula (I), or salt, or solvate thereof, preferably in the form of a pharmaceutical composition.

According to a further aspect of the seventh feature of the present invention there is provided a medicament comprising two or more fractions of doses of a compound of Formula (I), or salt, or solvate thereof, preferably in the form of a pharmaceutical composition, which together add up to a total daily dose, for administration in divided doses for use in a method of treatment of a human or animal body by therapy.

According to a further aspect of the seventh feature of the present invention there is provided a kit comprising two or more fractions of doses of a compound of Formula (I), or salt, or solvate thereof, preferably in the form of a pharmaceutical composition, which together add up to a total daily dose, for administration in divided doses.

According to a further aspect of the seventh feature of the present invention there is provided a kit comprising:

a) two or more fractions of doses of a compound of Formula (I), or salt, or solvate thereof, which together add up to a total daily dose, in unit dosage forms for administration in divided doses; and b) container means for containing said dosage forms.

According to a further aspect of the seventh feature of the present invention there is provided a kit comprising:

a) two or more fractions of doses of a compound of Formula (I), or salt, or solvate thereof, which together add up to a total daily dose, together with an excipient or carrier, in unit dosage forms; and b) container means for containing said dosage forms.

According to a further aspect of the seventh feature of the present invention there is provided the use of a compound of Formula (I), or salt, or solvate thereof, in the manufacture of a medicament for administration in divided doses for use in the production of a vascular damaging effect in a warm-blooded animal such as a human.

According to a further aspect of the seventh feature of the present invention there is provided the use of a compound of Formula (I), or salt, or solvate thereof, in the manufacture of a medicament for administration in divided doses for use in the production of an anti-cancer effect in a warm-blooded animal such as a human.

According to a further aspect of the seventh feature of the present invention there is provided the use of a compound of Formula (I), or salt, or solvate thereof, in the manufacture of a medicament for administration in divided doses for use in the production of an anti-tumour effect in a warm-blooded animal such as a human.

Divided doses, also called split doses, means that the total dose to be administered to a warm-blooded animal, such as a human, in any one day period (for example one 24 hour period from midnight to midnight) is divided up into two or more fractions of the total dose and these fractions are administered with a time period between each fraction of about greater than 0 hours to about 10 hours, preferably about 1 hour to about 6 hours, more preferably about 2 hours to about 4 hours. The fractions of total dose may be about equal or unequal.

Preferably the total dose is divided into two parts which may be about equal or unequal.

The time intervals between doses may be for example selected from: about 1 hour, about 1.5 hours, about 2 hours, about 2.5 hours, about 3 hours, about 3.5 hours, about 4 hours, about 4.5 hours, about 5 hours, about 5.5 hours and about 6 hours.

The time intervals between doses may be any number (including non-integers) of minutes between greater than 0 minutes and 600 minutes, preferably between 45 and 375 minutes inclusive. If more than two doses are administered the time intervals between each dose may be about equal or unequal.

Preferably two doses are given with a time interval in between them of greater than or equal to 1 hour and less than 6 hours.

More preferably two doses are given with a time interval in between them of greater than or equal to two hours and less than 5 hours.

Yet more preferably two doses are given with a time interval in between them of greater than or equal to two hours and less than or equal to 4 hours.

Particularly the total dose is divided into two parts which may be about equal or unequal with a time interval between doses of greater than or equal to about two hours and less than or equal to about 4 hours.

More particularly the total dose is divided into two parts which may be about equal with a time interval between doses of greater than or equal to about two hours and less than or equal to about 4 hours.

For the avoidance of doubt the term 'about' in the description of time periods means the time given plus or minus 15 minutes, thus for example about 1 hour means 45 to 75 minutes, about 1.5 hours means 75 to 105 minutes. Elsewhere the term 'about' has its usual dictionary meaning.

Although the compounds of the Formula (I) are primarily of value as therapeutic agents for use in warm-blooded animals (including man), they are also useful whenever it is required to inhibit and/or reverse and/or alleviate symptoms of angiogenesis and/or any disease state associated with angiogenesis. Thus, they are useful as pharmacological tools for use in the development of new biological tests and in the search for new pharmacological agents.

Biological Assay

Colchicine Binding Site Competitive Assay Kit.

The ability of a ligand to bind specifically to the colchicine binding site on tubulin, an indicator of the vascular damaging activity, was assessed using a size exclusion chromatography assay kit from "Cytoskeleton" (1650 Fillmore St. #240, Denver, Colo. 80206, U.S.A.) Catalogue number of kit: BK023.

The following reagents were used:
tubulin buffer, to give 0.1 mM GTP, 0.5 mM $MgCl_2$, 0.5 mM EGTA, 40 mM PIPES buffer at pH 6.9 in the final reaction mix;
purified tubulin protein from bovine brain at 1 mg/ml in tubulin buffer;
0.02 mM fluorescent colchicine in tubulin buffer [FITC (fluorescein isothiocyanate)-labelled];
2 mM colchicine in tubulin buffer;
0.2 mM vinblastine in tubulin buffer; and
G-25 Sephadex™ Fine-particle size 34–138 μm.

The reaction was performed as follows:

8 μl of test compound (dissolved in DMSO) was gently mixed with 150 μl of tubulin. This was then incubated at 37° C. for 30 minutes. Then 4 μl of the fluorescent colchicine was added, the incubation mix vortexed for 5 seconds and then incubated for a further 30 minutes at 37° C.

At the end of the reaction incubation size exclusion chromatography was performed to separate the tubulin with fluorescent colchicine bound from the free, unbound colchicine. If a test compound inhibited fluorescent colchicine binding then a reduced signal is measured and the compound is confirmed as a colchicine site binding moiety.

Chromatography was performed as follows, using chromatography columns filled with 3 mls of G-25 Sephadex™ Fine slurry. The incubation mixture was pipetted onto the column and up to 12 elutions of 160 μl were collected. The fluorescence of the tubulin-containing fractions was detected on a spectrophotometer which excites at 485 nm and emits at 535 nm.

Control incubations were also performed, 8 μl DMSO (negative control) and 8 μl colchicine stock (positive competition control), instead of the 8 μl of test compound in the incubation mixture.

The degree of competition of colchicine binding by either unlabelled colchicine or test compound was calculated relative to the DMSO negative control.

Compounds of Formula (I) encompass vascular damaging agents and pro-drugs of vascular damaging agents. Pro-drugs of vascular damaging agents are believed to be cleaved in-vivo. Without being bound by theoretical considerations these pro-drugs may have lower activity in the in-vitro colchicine binding site competitive assay, than would be anticipated when the activity of these compounds is measured in cell based assays or in-vivo.

The invention will now be illustrated with the following non-limiting Examples in which, unless otherwise stated:

(i) evaporations were carried out by rotary evaporation in vacuo and work-up procedures were carried out after removal of residual solids such as drying agents by filtration;

(ii) operations were carried out at ambient temperature, that is in the range 18–25° C. and under an atmosphere of an inert gas such as argon or nitrogen;

(iii) yields are given for illustration only and are not necessarily the maximum attainable;

(iv) the structures of the end-products of the Formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(v) intermediates were not generally fully characterised and purity was assessed by thin layer chromatography (TLC), high-performance liquid chromatography (HPLC), infra-red (IR) or NMR analysis;

(vi) flash chromatography was performed on silica (Merck Keiselgel: Art. 9385);

(vii) OASIS™ is a macroporous co-polymer, used to purify hydrophilic compounds, made from a balanced ratio of lipophillic divinylbenzene and hydrophillic N-vinylpyrrolidone. OASIS™ is described in the following patents, U.S. Pat. No. 5,882,521, U.S. Pat. No. 5,976,376 and U.S. Pat. No. 6,106,721. OASIS™ sample extraction products were obtained from Waters Corporation (Milford, Mass., USA).

| Abbreviations | |
|---|---|
| 4-Dimethylaminopyridine | DMAP |
| 1-(3-Dimethylaminopropyl)-3-ethylcarbodiimide hydrochloride | EDCI |
| Di-isopropyl ethylamine | DIEA |
| Dimethyl sulphoxide | DMSO |
| N-(9-fluorenylmethoxycarbonyl) | N-FMOC |
| N-methylpyrrolidine | NMP |

EXAMPLE 1

1-Methyl-2-carbamoyl-5-(3-aminobenzyloxy)-1H-indole

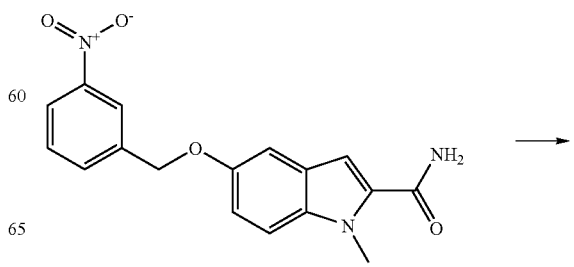

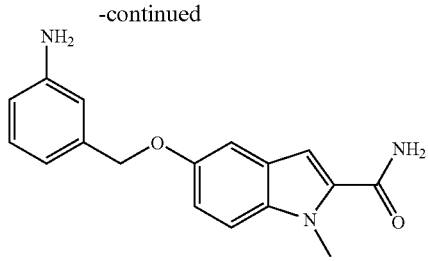

Example 1

A suspension of 1-methyl-2-carbamoyl-5-(3-nitrobenzyloxy)-1H-indole (1.22 g; 3.75 mmol), Pt O$_2$ (0.18 g) and K$_2$CO$_3$ (0.18 g) in methanol (120 ml) was hydrogenated under 45 psi for 1 hour.

The mixture was diluted with methanol, filtered on celite. After evaporation the residue was purified by flash chromatography eluting with CH$_2$Cl$_2$/CH$_3$CN/MeOH 46/46/8 to give 1-methyl-2-carbamoyl-5-(3-aminobenzyloxy)-1H-indole.

Yield: 70%
$^1$H NMR spectrum (DMSOd$_6$): 3.95 (s, 3H); 4.95 (s, 2H); 5.08 (bs, 2H); 6.49 (ddd, 1H); 6.58 (d, 1H); 6.65 (dd, 1H); 6.94–7.04 (m, 31H); 7.13 (d, 1H); 7.29 (bs, 1H); 7.42 (d, 1H); 7.88 (bs, 1H). MS-ESI: 296 [M+H]$^+$ The starting material was prepared as follows:

1-Methyl-2-carbamoyl-5-hydroxy-1H-indole

A suspension of 1-methyl-2-carbamoyl-5-benzyloxy-1H-indole (1.94 g; 6.96 mmol) and 10% Pd/C (0.5 g) in methanol (100 ml) was hydrogenated for 2 hours. After filtration of the catalyst on celite, the filtrate was evaporated to give 1-methyl-2-carbamoyl-5-hydroxy-1H-indole.

Yield: 95% $^1$H NMR spectrum (DMSOd$_6$): 3.92 (s, 3H); 6.79 (dd, 1H); 6.88 (d, 1H); 6.92 (s, 1H); 7.25 (bs, 1H); 7.31 (d, 1H); 7.83 (bs, 1H); 8.88 (bs, 1H).

1-Methyl-2-carbamoyl-5-(3-nitrobenzyloxy)-1H-indole

A mixture of 1-methyl-2-carbamoyl-5-hydroxy-1H-indole (0.875 g; 4.6 mmol), 2-nitrobenzyl bromide (1 g; 4.63 mmol) and Cs$_2$CO$_3$ (1.5 g; 4.63 mmol) in acetonitrile (55 ml) was heated at 90° C. under argon atmosphere for 2 h 30. After evaporation to dryness, the residue was extracted with CH$_2$Cl$_2$/H$_2$O. The organic phase was evaporated and the residue triturated in CH$_2$Cl$_2$/ether to give 1-methyl-2-carbamoyl-5-(3-nitrobenzyloxy)-1H-indole as a solid.

Yield: 86% $^1$H NMR spectrum (DMSOd$_6$): 3.96 (s, 3H); 5.30 (s, 2H); 7.03 (s, 1H); 7.05 (dd, 1H); 7.21 (d, 1H); 7.31 (bs, 1H); 7.46 (d, 1H); 7.71 (dd, 1H); 7.90 (bs, 1H); 7.94 (d, 1H); 8.19 (dd, 1H); 8.33 (s, 1H). MS-ESI: 326 [M+H]$^+$

EXAMPLE 2

2-Carbamoyl-5-(3-aminobenzyloxy)-1H-indole

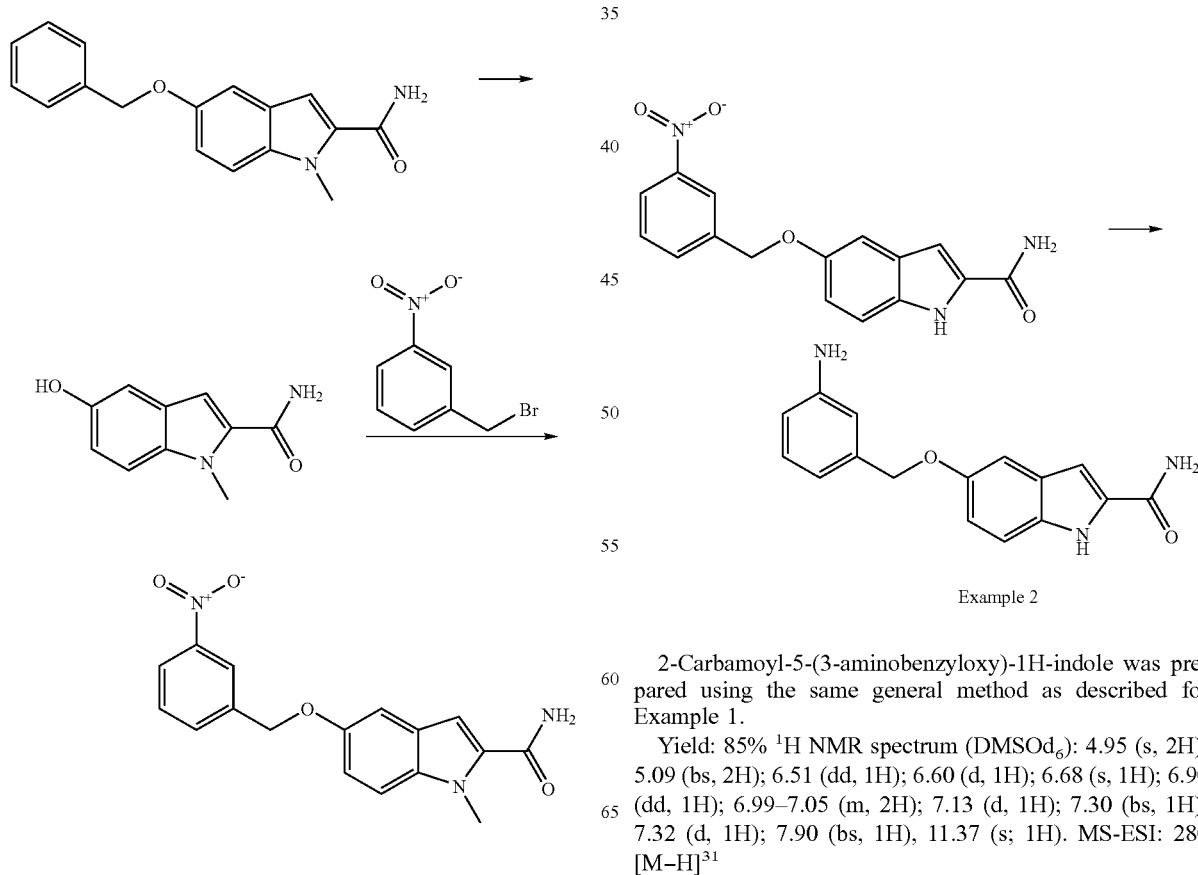

Example 2

2-Carbamoyl-5-(3-aminobenzyloxy)-1H-indole was prepared using the same general method as described for Example 1.

Yield: 85% $^1$H NMR spectrum (DMSOd$_6$): 4.95 (s, 2H); 5.09 (bs, 2H); 6.51 (dd, 1H); 6.60 (d, 1H); 6.68 (s, 1H); 6.90 (dd, 1H); 6.99–7.05 (m, 2H); 7.13 (d, 1H); 7.30 (bs, 1H); 7.32 (d, 1H); 7.90 (bs, 1H), 11.37 (s; 1H). MS-ESI: 280 [M–H]$^{31}$ The starting material was prepared as follows:

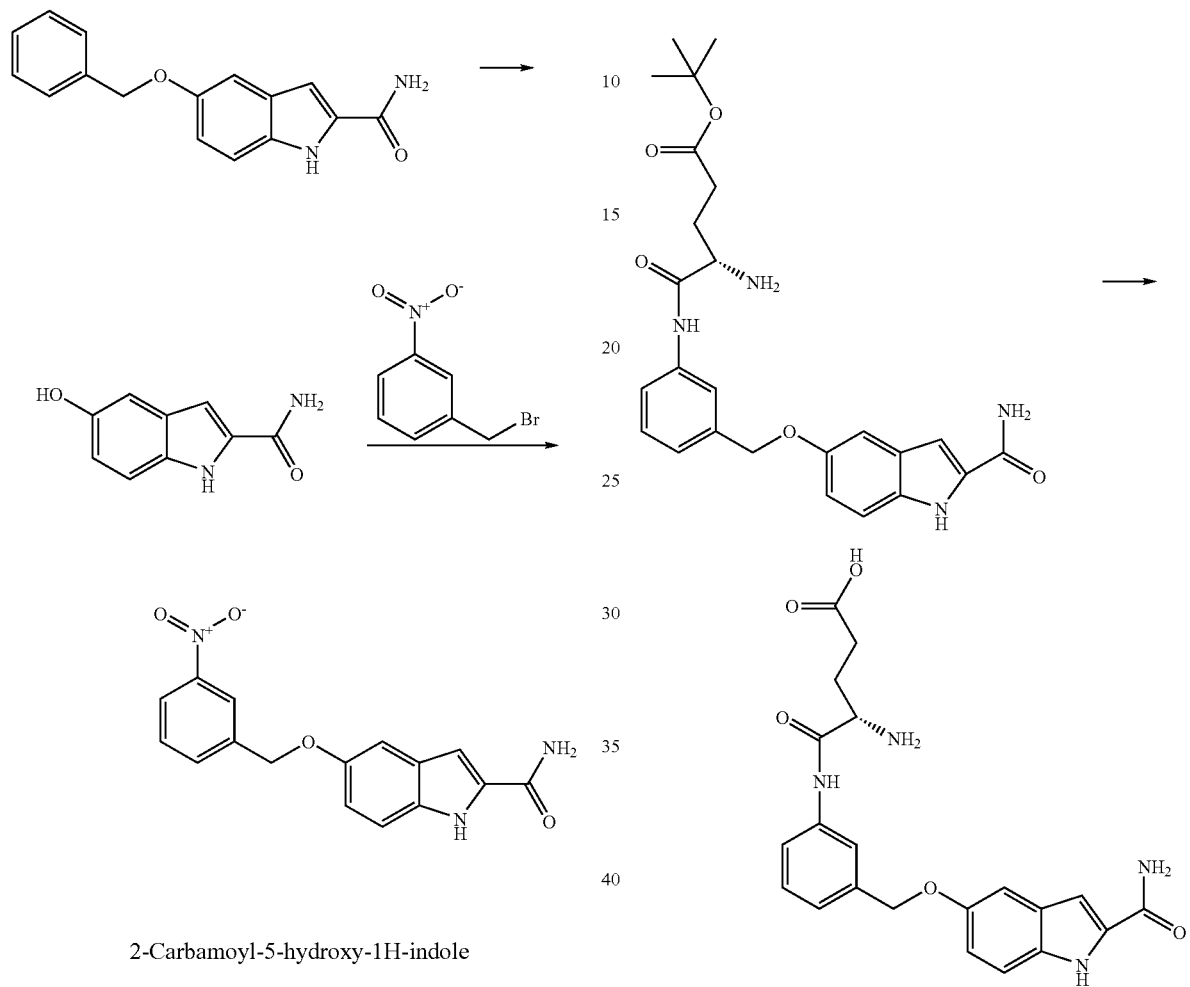

2-Carbamoyl-5-hydroxy-1H-indole

2-Carbamoyl-5-benzyloxy-1H-indole (1 g; 3.35 mmol) in solution in methanol (60 ml) was hydrogenated on 10% Pd/C (0.28 g) for 2 hours. After filtration on celite the solvent was evaporated to give 2-carbamoyl-5-hydroxy-1H-indole which was used in the next step without further purification.

Yield: 100%

$^1$H NMR spectrum (DMSOd$_6$): 6.71 (dd, 1H); 6.86 (d, 2H); 7.20 (d, 1H); 7.24 (bs, 1H); 7.81 (bs, 1H); 8.77 (bs, 1H); 11.20 (bs, 1H).

2-Carbamoyl-5-(3-nitrobenzyloxy)-1H-indole

This was prepared using the same general method as described in Example 1.

Yield: 38% $^1$H NMR spectrum (DMSOd$_6$): 5.27 (d, 2H); 6.96 (dd, 1H); 7.02 (s, 1H); 7.19 (d, 1H); 7.30 (bs, 1H); 7.34 (d, 1H); 7.70 (dd, 1H); 7.90 (bs, 1H); 7.94 (d, 1H); 8.19 (dd, 1H); 8.33 (s, 1H); 11.42 (bs, 1H).

EXAMPLE 3

2-Carbamoyl-5-[3-(α-glutamylamino)benzyloxy]-1H-indole

Example 3

2-Carbamoyl-5-[3-(O-tert-butyl-α-glutamylamino)benzyloxy]-1H-indole (0.29 g; 0.62 mmol) in solution in CH$_2$Cl$_2$ (2 ml) was treated under argon with HCl (2N) in dioxan (4 ml). The mixture was stirred for one hour, evaporated and the residue was purified on OASIS resin, eluting with H$_2$O/CH$_3$CN 80/20 to give 2-carbamoyl-5-[3-(α-glutamylamino)benzyloxy]-1H-indole.

Yield: 51% $^1$H NMR spectrum (DMSOd$_6$): 1.97–2.10 (m, 2H); 2.34–2.44 (m, 2H)); 3.94 (t, 1H); 5.10 (s, 2H); 6.91 (dd, 1H); 7.01 (d, 1H); 7.16 (d, 1H); 7.22 (d, 1H); 7.31 (bs, 1H); 7.32 (d, 1H); 7.37 (dd, 1H); 7.60 (d, 1H); 7.73 (s, 1H); 7.90 (bs, 1H); 8.96 (bs, 2H); 10.63 (bs, 1H); 11.41 (s, 1H).

| Elemental analysis | | C | H | N |
|---|---|---|---|---|
| | Found | C 54.54 | H 5.5 | N 12.45 |
| C$_{21}$H$_{22}$N$_4$O$_5$, 0.7 H$_2$O, 1 HCl | Requires | C 54.89 | H 5.35 | N 12.19 |

The starting material was prepared as follows:

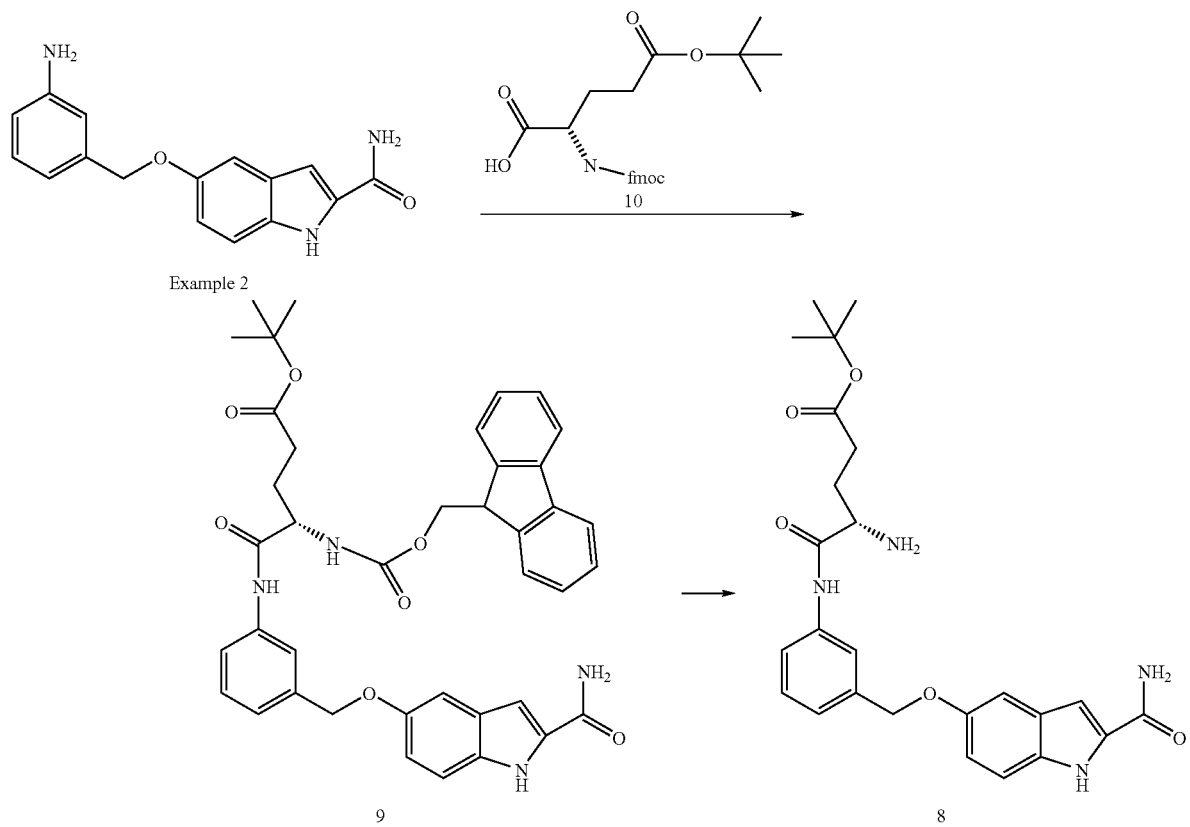

2-Carbamoyl-5-[3-(tert-butyl-α-glutamylamino)
benzyloxy]-1H-indole

A solution of 2-carbamoyl-5-(3-aminobenzyloxy)-1H-indole (Example 2) (0.28 g; 1 mmol) in CH₃CN (10 ml) was added to a solution of DIEA (0.191 ml; 1.1 mmol), HATU (0.418 g; 1.1 mmol) and 10 (0.467 g; 1.1 mmol) in CH₂Cl₂ (7 ml). The mixture was stirred overnight under argon atmosphere. After evaporation, the residue was purified by flash chromatography eluting with CH₂Cl₁ and CH₂Cl₂/Acetone 60/40 to give 9.

A solution of 9 (0.51 g; 0.74 mmol) and piperidine (0.8 ml) in CH₂Cl₂ (10 ml) was stirred at ambient temperature for 3 hours. After evaporation to dryness, the residue was purified by flash chromatography eluting with CH₂Cl₂, CH₂Cl₂/CH₃CN 90/10 and then with CH₂Cl₂/CH₃CN/MeOH 45/45/10 to give 2-carbamoyl-5-[3-(tert-butyl-α-glutamylamino)benzyloxy]-1H-indole.

Yield: 87% $^1$H NMR spectrum (DMSOd$_6$): 1.38 (s, 9H); 1.59–1.76 (m, 1H); 1.81–1.93 (m, 1H); 2.22–2.36 (m, 2H); 3.27–3.34 (m, 2H); 5.07 (s, 2H); 6.10 (dd, 1H); 7.01 (d, 1H); 7.12–7.18 (m, 2H); 7.26–7.35 (m, 3H); 7.59 (d, 1H); 7.77 (s, 1H); 7.88 (bs, 1H); 9.8 (bs, 2H); 11.38 (s, 1H).

EXAMPLE 4

1-Methyl-2-carbamoyl-5-[3-(α-glutamylamino)benzyloxy]-1H-indole

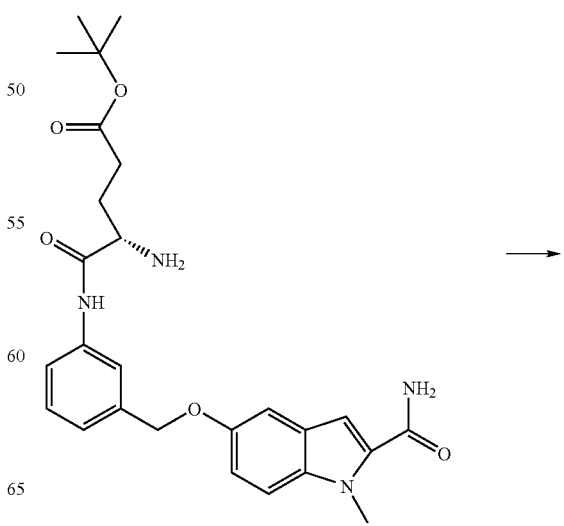

1-Methyl-2-carbamoyl-5-[3-(α-glutamylamino)benzyloxy]-1H-indole was prepared using the same general method as described for Example 3.

Yield: 81% $^1$H NMR spectrum (DMSOd$_6$): 2.02–2.12 (m, 2H); 2.36–2.44 (m, 2H); 3.97 (s, 3H); 4.01 (t, 1H); 5.12 (s, 2H); 7.00 (dd, 1H); 7.03 (s, 1H); 7.17 (d, 1H); 7.23 (d, 1H); 7.31 (bs, 1H); 7.38 (dd, 1H); 7.44 (d, 1H); 7.60 (d, 1H); 7.23 (s, 1H); 7.90 (bs, 1H); 8.83 (bs, 2H); 10.72 (s, 1H). MS-ESI: 423 [M−H]$^{31}$

| Elemental analysis | Found | C 55.04 | H 5.53 | N 11.49 |
|---|---|---|---|---|
| C$_{22}$H$_{24}$N$_4$O$_5$, 0.9 H$_2$O, 1 HCl | Requires | C 55.38 | H 5.66 | N 11.74 |

The starting material was prepared using analogous methodology to that described in Example 3 for the synthesis of 2-carbamoyl-5-[3-(tert-butyl-α-glutamylamino)benzyloxy]-1H-indole.

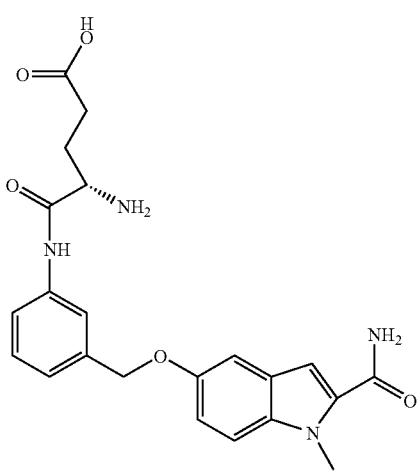

Example 4

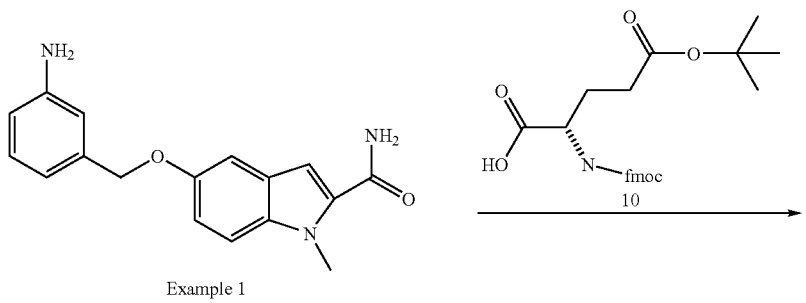

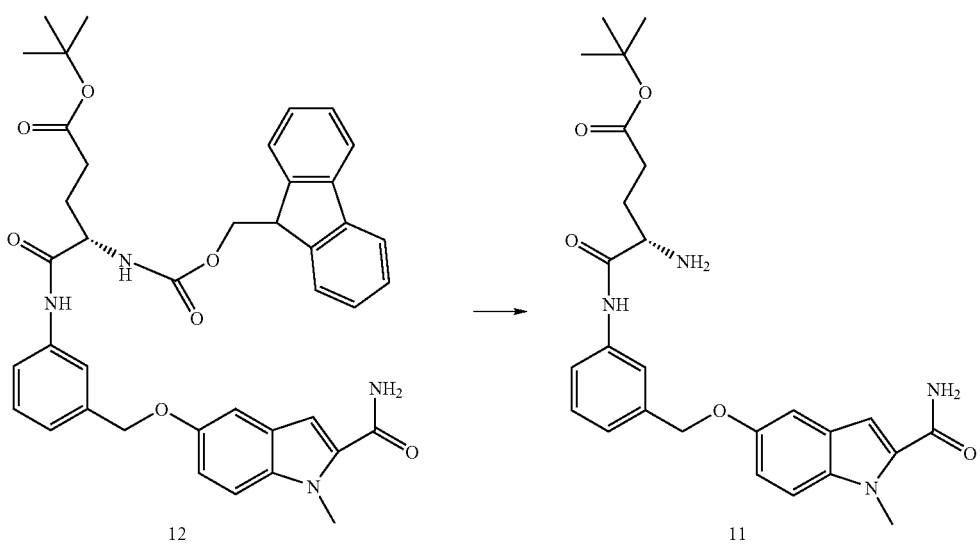

1-Methyl-2-carbamoyl-5-[3-(tert-butyl-α-glutamy-lamino)benzyloxy]-1H-indole

Yield: 75% (for the 2 steps) ¹H NMR spectrum (DMSOd6): 1.38 (s, 9H); 1.64–1.73 (m, 1H); 1.83–1.93 (m, 1H); 2.22–2.40 (m, 2H); 3.34–3.38 (m, 1H); 3.96 (s, 3H); 5.09 (s, 2H); 6.94-dd, 1H); 7.02 (s, 1H); 7.12–7.20 (m, 2H); 7.25–7.36 (m, 2H); 7.43 (d, 1H); 7.59 (d, 1H); 7.76 (s, 1H); 7.89 (bs, 1H); 10.0 (bs, 1H), 11.39 (s,1H). MS-ESI: 481 [M+H]⁺

EXAMPLE 5

3-Carbamoylmethyl-5-(3-aminobenzyloxy)-1H-indole

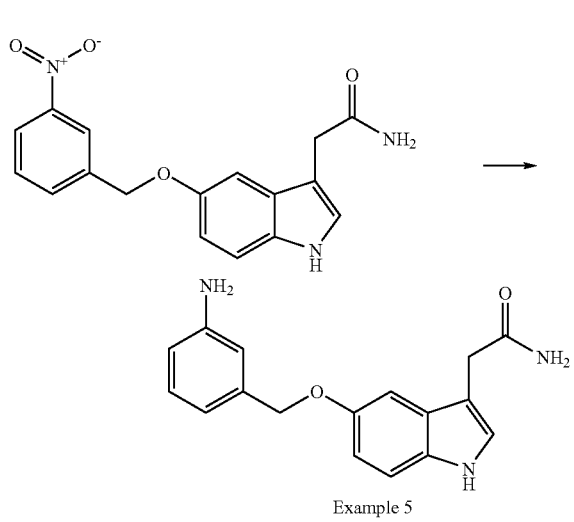

Example 5

3-Carbamoylmethyl-5-(3-aminobenzyloxy)-1H-indole was prepared using the same general method as described for Example 1.

Yield: 69% ¹H NMR spectrum (DMSOd₆): 3.43 (s, 2H)); 4.91 (s, 2H); 5.09 (bs, 2H); 6.51 (dd, 1H); 6.60 (d, 1H); 6.70 (s, 1H); 6.78 (dd, 1H); 6.82 (bs, 1H); 7.02 (dd, 1H); 7.17 (s,1H); 7.16 (d, 1H); 7.24 (d, 1H); 7.29 (bs, 1H); 10.71 (s, 1H). MS-ESI: 296 [M+H]⁺

The starting material was prepared using analogous methodology to that described in Example 1 for intermediate 1.

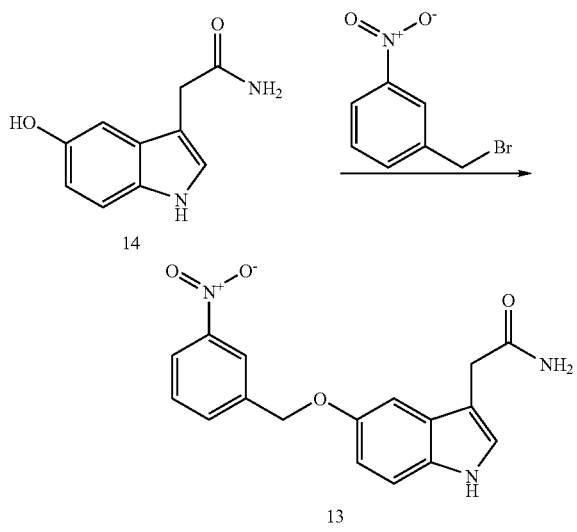

3-Carbamoylmethyl-5-(3-nitrobenzyloxy)-1H-indole

Yield: 58% ¹H NMR spectrum (DMSOd₆): 3.44 (s, 2H); 5.26 (d, 2H); 6.82 (bs, 1H); 6.87 (dd, 1H); 7.18 (d,1H); 7.20 (dd, 1H); 7.28 (bs, 1H); 7.28 (d, 1H); 7.72 (dd, 1H); 7.97 (d, 1H); 8.21 (dd, 1H); 8.36 (s, 1H); 10.77 (s, 1H). MS-ESI: 326 [M+H]⁺

EXAMPLE 6

3-Carbamoylmethyl-5-(3-α-glutamylbenzyloxy)-1H-indole

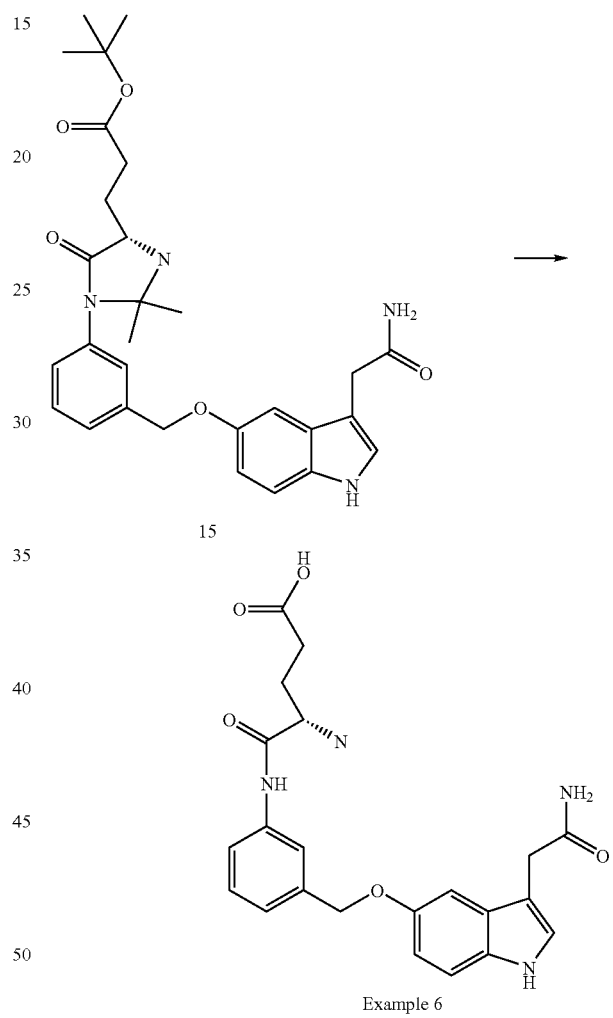

Example 6

3-Carbamoylmethyl-5-(3-α-glutamylbenzyloxy)-1H-indole was prepared using the same general method as described in Example 3 by deprotection of 15.

Yield: 27% ¹H NMR spectrum (DMSOd₆): 2.01–2.14 (m, 2H); 2.36–2.44 (m, 2H); 3.42 (s, 2H); 3.98–4.08 (m, 1H); 5.08 (s, 2H); 6.77–6.83 (m, 2H); 7.16 (dd, 1H); 7.18 (d, 1H); 7.21–7.27 (m, 2H); 7.30 (bs, 1H); 7.38 (dd, 1H); 7.61 (d, 1H); 7.74 (s, 1H); 8.37 (bs, 2H); 10.74 (s, 1H); 12.38 (bs, 1H). MS-ESI: 425 [M+H]⁺

The starting material 15 was prepared using analogous method to that described in Example 3 starting from 3-carbamoylmethyl-5-(3-aminobenzyloxy)-1H-indole (Example 5).

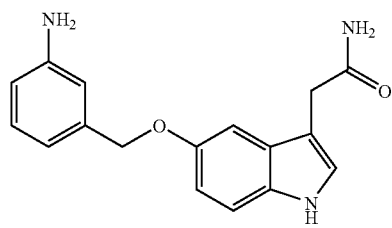

Example 5

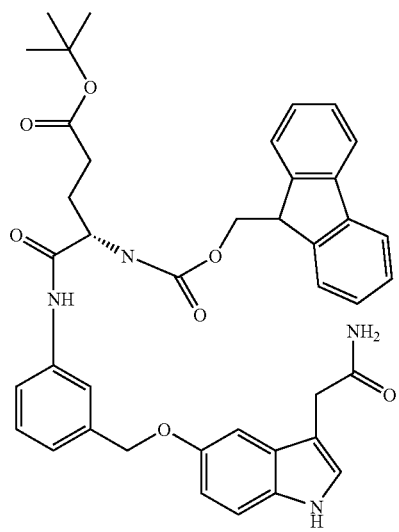

16

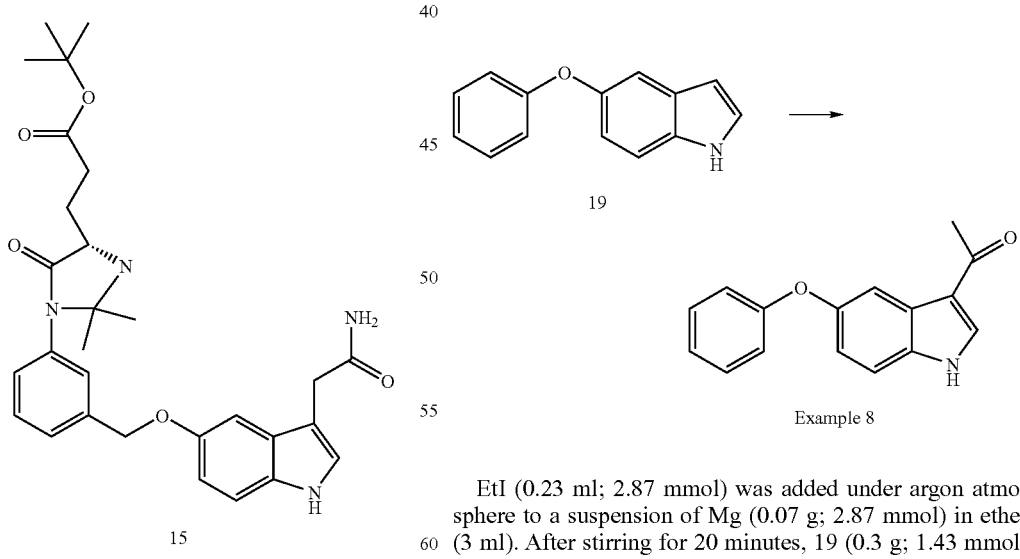

15

Yield: 45.9% ¹H NMR spectrum (DMSOd$_6$) 1.26 (s, 3H); 1.30 (s, 3H); 1.42 (s, 9H); 1.65–1.78 (m, 1H); 1.93–2.05 (m, 1H); 2.30–2.45 (m, 2H); 3.41 (s, 2H); 3.54–3.62 (m, 1H); 5.10 (m, 2H); 6.79 (bs, 1H); 6.81 (dd, 1H); 7.10–7.31 (m, 6H); 7.46–7.49 (m, 2H)); 10.71 (s, 1H).

EXAMPLE 7

2-Carbamoyl-6-benzyloxy-1H-indole

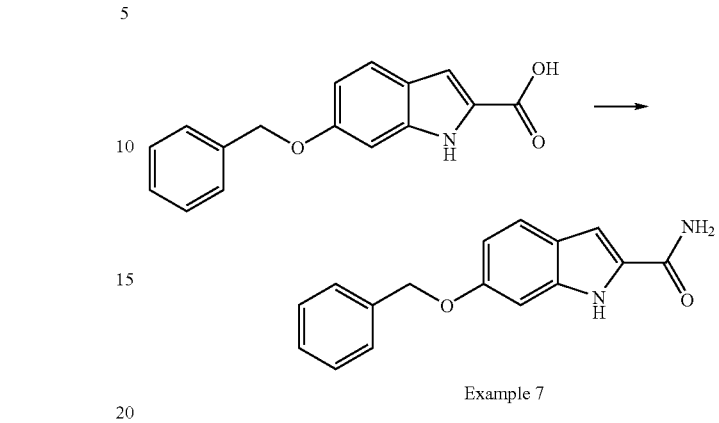

Example 7

A solution of 2-carboxy-6-benzyloxy-1H-indole (0.125 g; 0.468 mmol), oxalyl chloride (0.5 mmol) and DMF (0.2 ml) in CH$_2$Cl$_2$ was stirred at room temperature for 2 hours. After evaporation to dryness, the residue was redissolved in acetone; ammonium acetate (0.074 g; 0.95 mmol) was added to the solution and the mixture was stirred at room temperature for 1 hour. After evaporation, the residue was purified by flash chromatography eluting with CH$_2$Cl$_2$/acetone 80/20 to give 2-carbamoyl-6-benzyloxy-1H-indole.

Yield: 70% ¹H NMR spectrum (DMSOd$_6$): 5.10 (s, 2H); 6.77 (dd, 1H); 6.96 (d, 1H); 7.04 (d, 1H); 7.21 (bs, 1H); 7.33 (t, 1H); 7.40 (t, 2H); 7.46–7.50 (m, 3H); 7.82 (bs, 1H); 11.34 (s, 1H). MS-ESI: 265 [M–H]⁻

EXAMPLE 8

2-Acetyl-5-phenoxy-1H-indole

19

Example 8

EtI (0.23 ml; 2.87 mmol) was added under argon atmosphere to a suspension of Mg (0.07 g; 2.87 mmol) in ether (3 ml). After stirring for 20 minutes, 19 (0.3 g; 1.43 mmol) in solution in ether (7 ml) was added. The mixture was stirred for 1 hour, cooled to 10° C. and acetyl chloride (0.113 ml; 1.58 mmol) was added. After stirring at 10° C. for 30 minutes, the mixture was poured in ether/H$_2$O. The organic phase was evaporated and purified by flash chromatography eluting with petroleum ether/AcOEt 60/40 to give 2-acetyl-5-phenoxy-1H-indole.

Yield: 30% ¹H NMR spectrum (DMSOd₆): 2.41 (s, 3H); 6.94 (d, 2H); 6.97 (dd, 1H); 7.07 (t, 1H); 7.35 (dd, 2H); 7.49 (d, 2H); 7.75 (d, 1H); 8.34 (d, 1H); 11.99 (bs, 1H). MS-ESI: 250 [M–H]⁻

EXAMPLE 9

3-Methoxycarbonyl-5-phenylsulphanyl-1H-indole

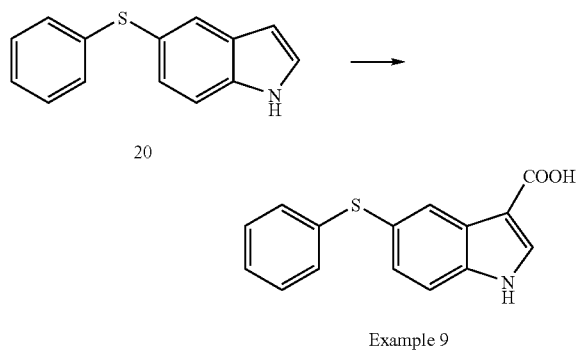

Example 9

Mg (0.073 g; 3 mmol) was added under argon atmosphere to a solution of EtI (0.240 ml; 3 mmol) in ether (4 ml). After stirring for 20 minutes, 20 (0.338 g; 1.5 mmol) in solution in ether (5 ml) was added. The mixture was cooled to 10° C. and methyl chloroformate (0.128 ml; 1.65 mmol) was added. After stirring for 15 minutes, the mixture was extracted with AcOEt/H₂O. The organic phase was evaporated to give 3-methoxycarbonyl-5-phenylsulphanyl-1H-indole after purification by flash chromatography and elution with petroleum ether/AcOEt 95/5.

Yield: 28% ¹H NMR spectrum (DMSOd₆): 3.80 (s, 3H); 7.12–7.21 (m, 3H); 7.26–7.32 (m, 3H); 7.56 (d, 1H); 8.13–8.18 (m, 1H); 12.15 (bs, 1H). MS-ESI: 282 [M–H]⁻

EXAMPLE 10

3-Cyano-5-phenylsulphanyl-1H-indole

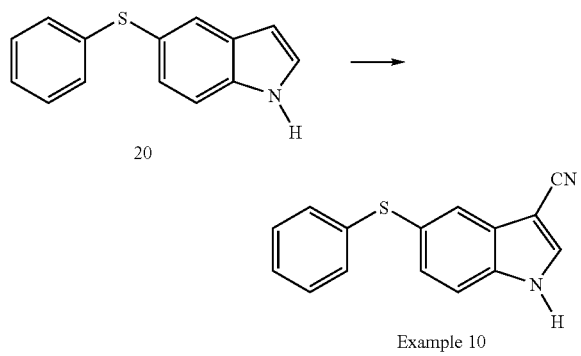

Example 10

To a stirred solution of 20 (0.45 g; 2 mmol) in CH₃CN (6 ml) at 0° C. was added chlorosulfonyl isocyanate (0.175 ml; 2 mmol) in solution in CH₃CN (6 ml). Et₃N (0.272 ml; 1.96 mmol) was added over 45 minutes, maintaining the temperature near 0° C. The resulting solution was stirred at room temperature for 2 hours. The solvent was removed and the residue extracted with CH₂Cl₂/sat. aq. NaHCO₃. The organic phase was purified by flash chromatography eluting with CH₂Cl₂/EtOH 98/2 to give after trituration in ether 3-cyano-5-phenylsulphanyl-1H-indole as a solid.

Yield: 38% ¹H NMR spectrum (CDCl₃): 7.16–7.23 (m, 1H); 7.25–7.29 (m, 4H); 7.38–7.46 (m, 2H); 7.75 (d, 1H); 7.90 (s, 1H); 8.75 (bs, 1H).

EXAMPLE 11

3-Cyano-5-phenoxy-1H-indole

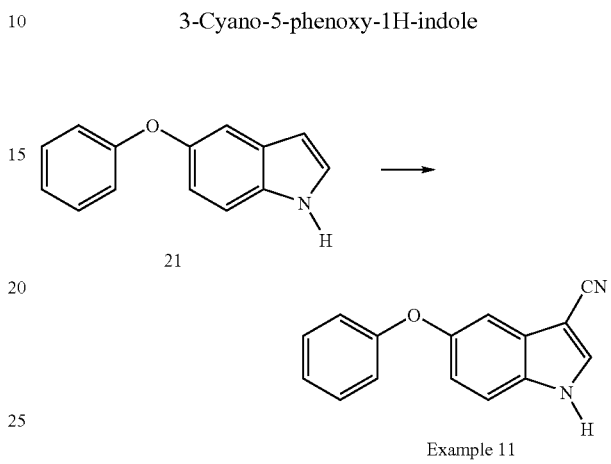

Example 11

3-Cyano-5-phenoxy-1H-indole was prepared using the same method as described for Example 10 but starting from 21.

Yield: 62% ¹H NMR spectrum (DMSOd₆): 6.99 (d, 2H); 7.04 (d, 1H); 7.12 (t, 1H); 7.16 (d, 1H) 7.38 (dd, 2H); 7.58 (d, 1H); 8.27 (s, 1H); 12.22 (bs, 1H). MS-ESI: 233 [M–H]⁻

EXAMPLE 12

3-Carbamoyl-5-phenoxy-1H-indole

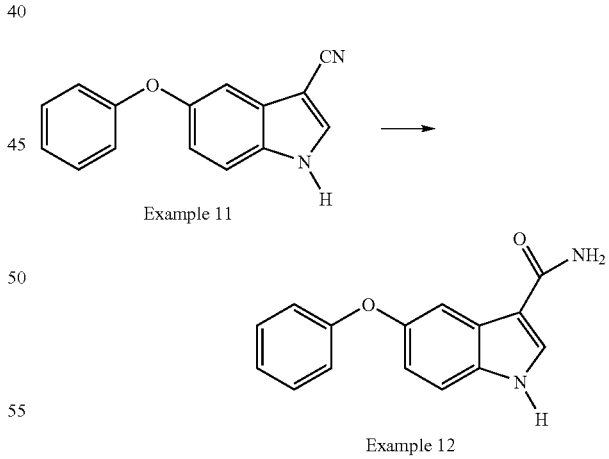

Example 12

To a solution of 3-Cyano-5-phenoxy-1H-indole (Example 11) (0.105 g; 0.45 mmol) in EtOH (3 ml) and 1N NaOH (1.5 ml) was added H₂O₂ (0.15 ml). The mixture was heated at 50° C. for 1 h 30 mn, diluted with water, cooled to 5° C. and neutralised to pH 7 with 1N HCl.

The mixture was extracted with AcOEt, evaporated to dryness and purified by flash chromatography, eluting with petroleum ether/AcOEt 50/50 to give 3-carbamoyl-5-phenoxy-1H-indole.

Yield: 35% ¹H NMR spectrum (DMSOd₆): 6.77 (bs, 1H); 6.89–6.96 (m, 3H); 7.05 (dd, 1H); 7.34 (dd, 2H); 7.40 (bs, 1H); 7.45 (d, 1H); 7.76 (d, 1H); 8.06 (d, 1H); 11.59 (bs, 1H). MS-ESI: 253 [M–H]⁻

EXAMPLE 13

3-Carbamoyl-5-(4-hydroxyphenoxy)-1H-indole

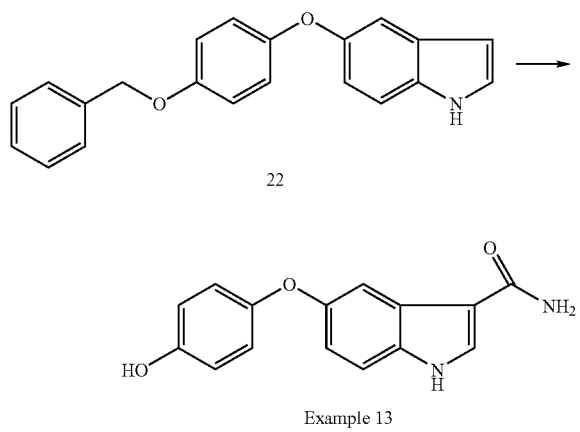

Example 13

To a stirred solution of 22 (0.25 g; 0.79 mmol) in ether (10 ml) at 0° C. was added chlorosulphonyl isocyanate (0.561 g; 3.9 mmol). The solution was stirred for 20 minutes. The precipitate was collected by filtration, redissolved in THF (3 ml) and exposed to light for 30 minutes. After evaporation, the residue was taken up in methanol (5 ml). Ammonium acetate (0.498 g; 0.79 mmol) and Pd/C (0.05 g) were added. The suspension was heated to 80° C. for 30 minutes. After filtration and trituration with water, the solid was washed with ether to give 3-carbamoyl-5-(4-hydroxyphenoxy)-1H-indole.

Yield: 52% ¹H NMR (DMSOd₆): 6.84 (m, 5H); 7.42 (dd, 1H); 7.65 (m, 1H); 8.08 (s, 1H). MS-ESI: 267 [M–H]⁻

The starting material was prepared as follows:

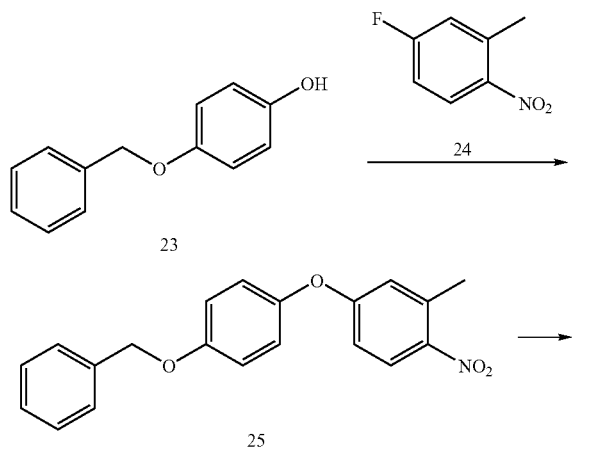

-continued

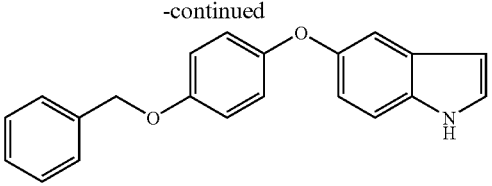

22

2-Methyl-4-(4-benzyloxyphenoxy)-nitrobenzene

To a stirred slurry of 23 (25 g; 124.9 mmol) and K₂CO₃ (34.5 g; 249.8 mmol) in NMP (100 ml) was added 5-fluoro-2-nitrotoluene (19.56 g; 126.1 mmol). The mixture was heated to 180° C. for 2 hours. The suspension was cooled to room temperature and the product was precipitated into water (300 ml). The solid was filtered and purified by flash chromatography eluting with heptane/CH₂Cl₂ 50/50 to give 2-methyl-4-(4-benzyloxyphenoxy)-nitrobenzene (25).

Yield: 93% ¹H NMR (DMSOd₆): 3.32 (s, 3H); 5.11 (s, 2H); 6.86 (m, 1H); 6.99 (m, 1H); 7.11 (m, 5H); 7.3–7.5 (m, 5H).

3-Carbamoyl-5-(4-benzyloxyphenoxy)-1H-indole

To a stirred solution of 25 (40 g; 119.4 mmol) and pyrrolidine (8.49 g; 119.4 mmol) in dry DMF (40 ml) was added N,N-dimethyl formamide dimethyl acetal (42.7 g; 3.58 mmol). The mixture was heated to 120° C. for 2 hours and extracted with ether/H₂O. The organic phase was evaporated to give a red solid. 40 g of the solid in solution in toluene-acetic acid (500 ml; 3:2) were added to a stirred suspension of Fe (80 g; 1.43 mol) and silica gel (130 g) in a mixture of toluene-acetic acid (1.5 l; 3:2). The reaction mixture was heated to 100° C. for 1 hour. The suspension was cooled to ambient temperature and filtered through celite. The filtrate was concentrated to afford an oil which was purified by flash chromatography, eluting with heptane/CH₂Cl₂ 50/50 to give 22.

Yield: 43% ¹H NMR (DMSOd₆): 5.05 (s, 2H); 6.36 (m, 1H); 6.80 (dd, 1H); 6.89 (d, 2H); 6.97 (d, 2H); 7.09 (m, 1H); 7.39 (m, 7H). MS-ESI: 316 [M+H]⁺

EXAMPLE 14

3-Carbamoyl-5-(4-phosphonoxyphenoxy)-1H-indole

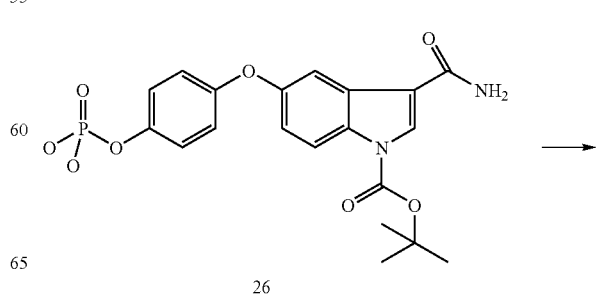

26

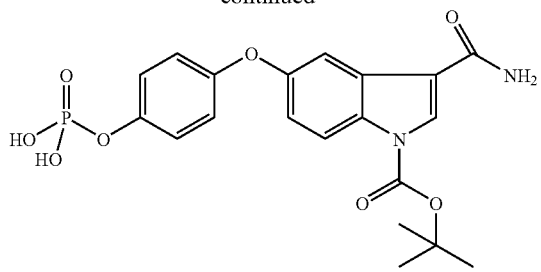

Example 14

To a mixture of 1-tert-butyloxycarbonyl-3-carbamoyl-5-(4-phosphonoxyphenoxy)-1H-indole (26) (0.47 g; 1 mmol) in CH$_2$Cl$_2$ was added TFA (25 ml). The solution was stirred for 2 hours. The solvent was evaporated and the solid purified on Oasis resin eluting with a 0–30% gradient MeOH/H$_2$O. After evaporation of methanol, the pH was adjusted to 7.5 with 0.1N NaOH to give after freeze drying 3-carbamoyl-5-(4-phosphonoxyphenoxy)-1H-indole.

Yield: 80% $^1$H NMR (DMSOd$_6$): 6.83 (m, 3H); 7.16 (d, 2H); 7.45 (d, 1H); 7.75 (s, 1H); 8.09 (s, 1H). MS-ESI: 349 [M+H]$^{-+}$ The starting material was prepared as follows:

1-tert-Butyloxycarbonyl-3-carbamoyl-5-(4-benzyloxyphenoxy)-1H-indole

To a stirred solution of 27 (2 g; 5.6 mmol) in acetonitrile (100 ml) were added DMAP (0.034 g; 0.28 mmol) and di-tert-butyldicarbonate (1.22 g; 5.6 mmol). The suspension was stirred for 1 hour. The solvent was evaporated and the residue taken up in AcOEt (100 ml), washed with 10% citric acid and purified by flash chromatography eluting with CH$_2$Cl$_2$/MeOH 95/5 to give 28.

Yield: 61% $^1$H NMR (DMSO): 1.66 (s, 9H); 5.09 (s, 2H); 7.05 (m, 5H); 7.14 (brs, 1H); 7.41 (m, 3H); 7.47 (d, 2H); 7.75 (m, 1H); 7.86 (brs, 1H); 8.05 (d, 1H); 8.48 (s, 1H). MS-ESI: 459 [M+H]$^+$

1-tert-Butyloxycarbonyl-3-carbamoyl-5-(4-hydroxyphenoxy)-1H-indole

To a solution of 28 (1.39 g; 2.8 mmol) in AcOEt/EtOH (1:2; 150 ml), 10% Pd/C (0.6 g) was added and the suspension was hydrogenated for 2 hours. After filtration on celite the filtrate was evaporated to dryness to give 29.

Yield: 98% $^1$H NMR (DMSO): 1.64 (s, 9H); 6.78 (2H, d); 6.88 (d, 2H); 7.05 (dd, 1H); 7.11 (brs, 1H); 7.69 (m, 1H); 7.80 (brs, 1H); 7.99 (dd, 1H); 8.45 (s, 1H); 9.30 (brs, 1H). MS-ESI: 367 [M+H]$^+$

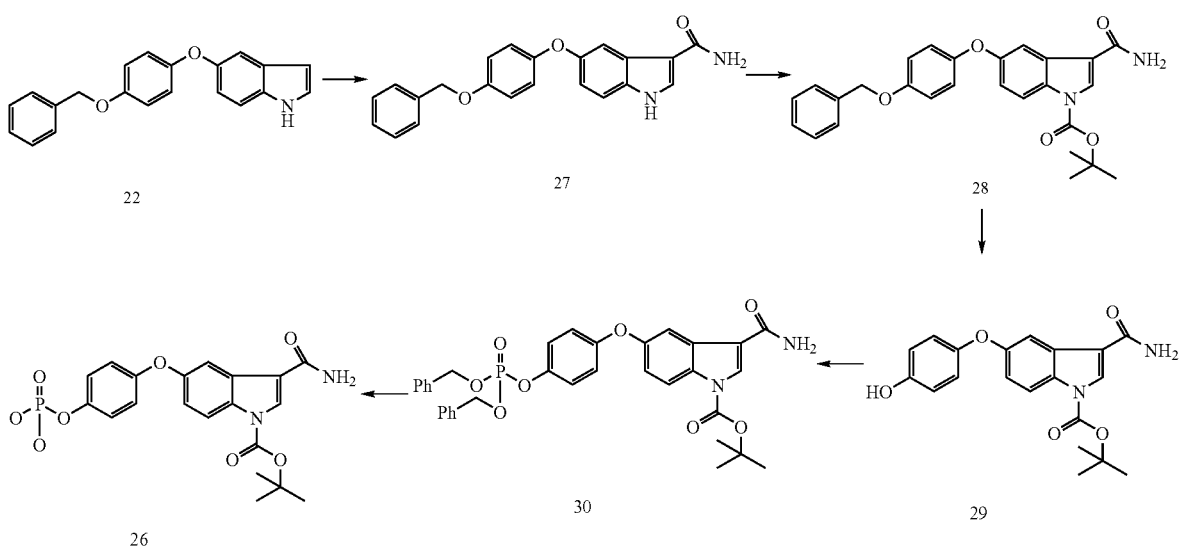

3-Carbamoyl-5-(4-benzyloxyphenoxy)-1H-indole

To a stirred solution of 23 (2 g; 6.3 mmol) in ether (100 ml) at 0° C. was added chlorosulphonyl isocyanate (4.49 g; 32 mmol). The solution was stirred at 0° C. for 1 hour. The solid was collected by filtration and dissolved in THF (20 ml). The solution was exposed to light for 1 hour. After evaporation the residue was purified by flash chromatography eluting with CH$_2$Cl$_2$/MeOH 85/15 to give 27.

Yield: 94% $^1$H NMR (DMSO): 5.08 (s, 2H); 6.88 (m, 3H); 7.04 (d, 12H); 7.41 (m, 5H); 7.67 (m, 1H); 8.05 (m, 1H). MS-ESI: 359 [M+H]$^+$

1-tert-Butyloxycarbonyl-3-carbamoyl-5-[4-(di-benzyloxy-phosphonoxy)phenoxy]-1H-indole To a stirred solution of 29 (1.03 g; 2.8 mmol), CCl$_4$ (4.31 g; 28 mmol), DIPEA (1.81 g; 14 mmol) and DMAP (0.02 g) in acetonitrile (10 ml) at 0° C. was added dibenzyl phosphite (4.41 g; 16.8 mmol) over a period of 30 minutes. The mixture was allowed to warm to room temperature and stirred for 1 hour. After evaporation, the residue was taken up in CH$_2$Cl$_2$ (200 ml), washed with 10% citric acid. The organic layer was evaporated and purified by flash chromatography eluting with CH$_2$Cl$_2$/AcOEt 50/50 to give 30.

Yield: 63% ¹H NMR (DMSOd₆): 1.67 (s, 9H); 5.19 (s, 4H)); 7.00 (d, 2H); 7.12 (dd, 1H); 7.20 (d, 2H); 7.39 (9H, m); 7.85 (d, 1H); 8.10 (d, 2H); 8.52 (s, 1H). MS-ESI: 629 [M+H]⁺

1-tert-Butyloxycarbonyl-3-carbamoyl-5-(4-phosphonoxyphenoxy)-1H-indole

To a stirred solution of 30 (1.1 g; 1.8 mmol) in AcOEt/EtOH (30 ml; 1:1) was added 10% Pd/C (0.2 g). The suspension was hydrogenated for 1 hour. After filtration of the catalyst the solvent was evaporated to give 26 as a foam.

Yield: 58% ¹H NMR (DMSOd₆): 1.65 (s, 9H); 6.99 (d, 2H); 7.10 (dd, 1H); 7.14 (d, 2H); 7.91 (m, 1H); 7.97 (brs, 1H); 8.07 (d, 1H); 8.49 (s, 1H).
MS-ESI: 449 [M+H]⁺

EXAMPLE 15

3-Cyano-5-(4-hydroxyphenoxy)-1H-indole

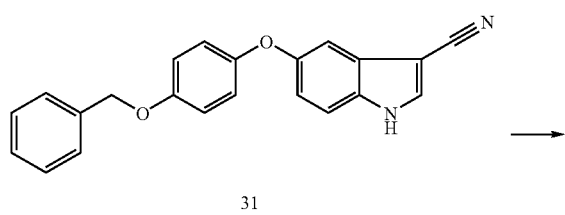

31

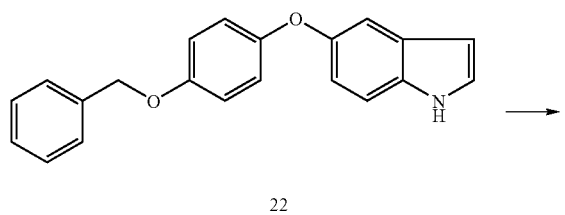

Example 15

To a stirred solution of 31 (0.2 g; 0.6 mmol) in AcOEt/EtOH (1:1; 100 ml) was added 10% Pd/C (0.05 g). The suspension was hydrogenated for 1 hour. After filtration and evaporation, the residue was purified by flash chromatography eluting with CH₂Cl₂/MeOH 95/5 to give 3-cyano-5-(4-hydroxyphenoxy)-1H-indole.

Yield: 100% ¹H NMR (DMSOd₆): 6.78 (m, 3H); 6.89 (d, 2H); 6.96 (m, 2H); 7.53 (dd, 1H); 8.22 (s, 1H). MS-ESI: 249 [M+H]⁺

The starting material was prepared as follows:

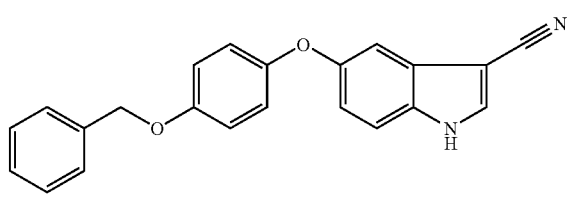

22

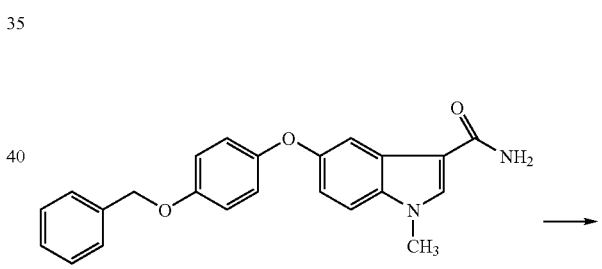

31

3-Cyano-5-(4-benzyloxyphenoxy)-1H-indole

To a stirred suspension of 22 (0.36 g; 1.14 mmol) in ether (20 ml) was added chlorosulphonyisocyanate (0.80 g; 5.7 mmol) at 0° C. The mixture was stirred for 1 hour at 0° C. The resulting solid was collected by filtration, redissolved in THF (20 ml) and exposed to light for 1 hour. After evaporation, the residue was purified by flash chromatography eluting with CH₂Cl₂ to give 31 as the by product.

Yield: 17% ¹H NMR (DMSO) 5.06 (s, 2H); 6.92 (m, 3H); 6.98 (d, 2H); 7.39 (m, 6H); 7.68 (m, 1H); 8.04 (m, 1H). MS-ESI: 339.53 [M+H]⁺

EXAMPLE 16

1-Methyl-3-carbamoyl-5-(4-hydroxyphenoxy)-1H-indole

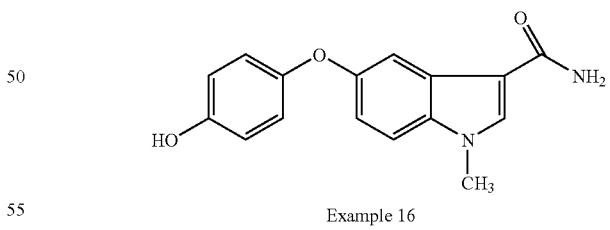

32

Example 16

To a stirred solution of 32 (0.2 g; 0.5 mmol) in EtOH (50 ml) was added Pd(OH)₂ (0.05 g). The suspension was hydrogenated for 1 hour. After filtration and evaporation, the residue was purified by flash chromatography eluting with CH₂Cl₂/MeOH to give 1-methyl-3-carbamoyl-5-(4-hydroxyphenoxy)-1H-indole.

Yield: 53% ¹H NMR (DMSO): 3.82 (s, 3H); 6.74 (d, 2H); 6.82 (d, 2H); 6.91 (dd, 1H); 7.48 (dd, 1H); 7.66 (dd, 1H); 7.98 (s, 1H); 9.21 (s, 1H). MS-ESI: 281 [M−H]⁻

The starting material was prepared as follows

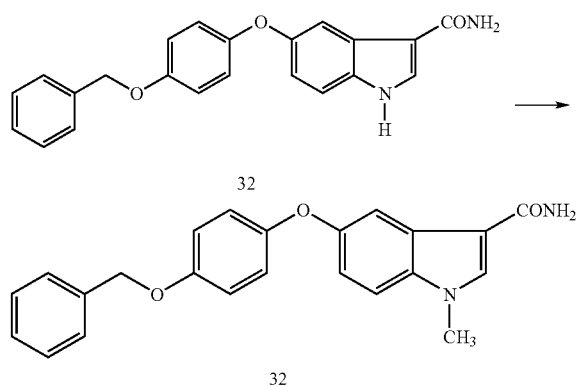

1-Methyl-3-carbamoyl-5-(4-benzyloxyphenoxy)-1H-indole

To a stirred solution of 27 (0.26 g; 0.76 mmol) in THF (3 ml), at 0° C. was added NaH (0.032 g; 0.8 mmol). MeI (0.108 g; 0.76 mmol) was added. The reaction was stirred at room temperature for 1 hour. After evaporation the residue was purified by flash chromatography, eluting with $CH_2Cl_2$/MeOH 90/10 to give 32.

Yield: 70% $^1$H NMR (DMSO): 3.81 (s, 3H); 5.07 (s, 2H); 6.91 (m, 3H); 6.99 (d, 2H); 7.39 (m, 6H); 7.68 (m, 1H); 7.98 (s, 1H). MS-ESI: 373 [M+H]$^+$

EXAMPLE 17

2-Cyano-5-benzyloxy-1H-indole

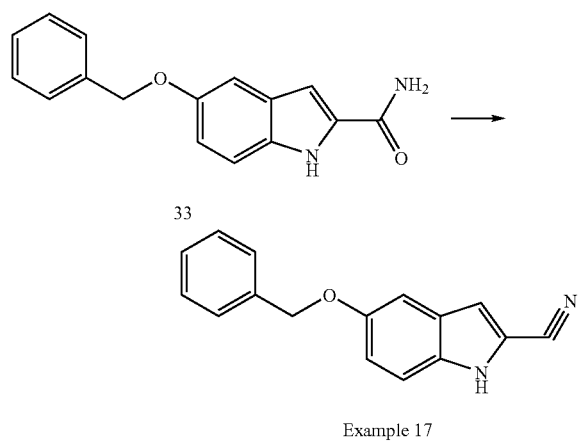

Trichloromethylchloroformate (0.087 ml; 0.72 mmol) was added to 33 (0.12 g; 0.451 mmol) and trimethyl phosphite (0.21 ml). The mixture was heated at 60° C. for 5 minutes, diluted with water and extracted with ether. The organic phase was evaporated, the residue was purified by flash chromatography, eluting with $CH_2Cl_2$ to give 2-cyano-5-benzyloxy-1H-indole.

Yield: 62% $^1$H NMR spectrum (DMSOd$_6$): 5.11 (s, 2H); 7.07 (dd, 1H); 7.21 (d, 1H); 7.23 (d, 1H); 7.33 (dd, 1H); 7.36–7.43 (m, 3H); 7.47 (d, 2H); 12.25 (bs, 1H). MS-ESI: 247 [M−H]$^−$

EXAMPLE 18

1-Methyl-3-cyano-5-(4-hydroxy-3,5-dimethoxyphenoxy)-1H-indole

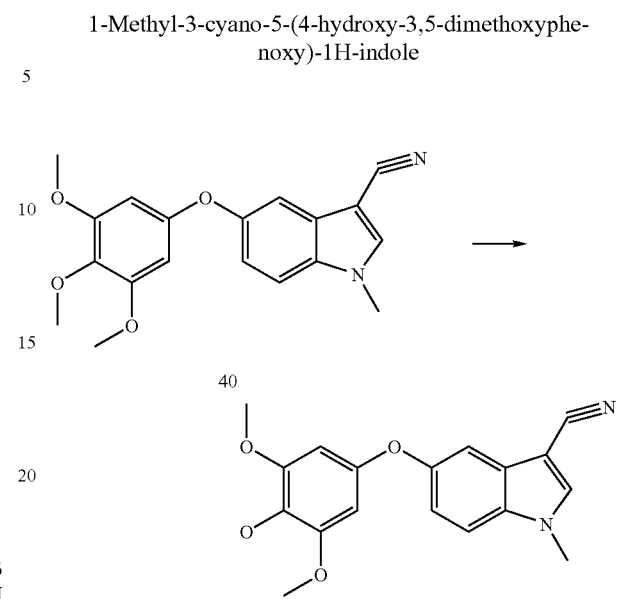

Example 18

To a solution of 1-methyl-3-cyano-5-(3,4,5-trimethoxyphenoxy)-1H-indole (500 mg; 1.47 mmol) in $CH_2Cl_2$ (10 ml) was added trimethylsilyl iodide (831 μl; 5.84 mmol). After stirring at room temperature under argon atmosphere for 2 h30, the mixture was poured into cold water, extracted with ethyl acetate. The organic phase was evaporated and the residue was purified by flash chromatography on silica gel, eluting with $CH_2Cl_2$/Et$_2$O 1:1 to give 1-methyl-3-cyano-5-(4-hydroxy-3,5-dimethoxyphenoxy)-1H-indole: (244 mg)

| Elemental analysis | | | | |
|---|---|---|---|---|
| $C_{18}H_{16}N_2O_4$ | Found | C 66.19 | H 4.98 | N 8.47 |
| | Requires | C 66.66 | H 4.97 | N 6.64 |

The starting material was prepared as follows:

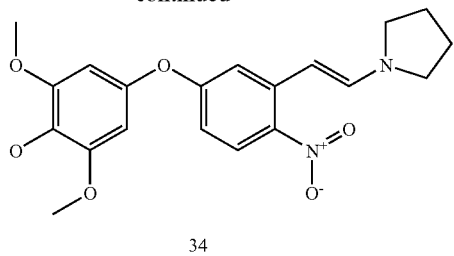

34

2-Methyl-4-(3,4,5-trimethoxyphenoxy)-nitrobenzene

A solution of 35 (6 g; 32.5 mmol), 36 (5.0 g; 32.5 mmol) and $K_2CO_3$ (6.7 g; 48.5 mmol) in NMP (65 ml) was heated at 80° C. under argon atmosphere for 3 h. After cooling, the mixture was poured on cold water and the precipitate was filtrated, washed with water then pentane, and purified by flash chromatography, eluting with $CH_2Cl_2$ to give 37 as a yellow solid: 9.3 g Yield: 90%. $^1$H NMR spectrum (DMSOd6): 2.55 (s, 3H); 3.68 (s, 3H); 3.72 (s, 6H); 6.53 (s, 2H); 6.95 (dd, 1H); 7.07 (d, 1H); 8.07 (d, 1H).

To a solution of 37 (9.3 g; 29.15 mmol) in DMF (15 ml) was added N,N-Dimethylformamide dimethyl acetal (4.5 ml; 33.8 ml) and pyrrolidine (2.8 ml; 33.8 mmol). The solution was heated at reflux (110° C.) under argon atmosphere for 2 h30. After evaporation under vacuum, the residue was dissolved in $CH_2Cl_2$ (8 ml) and Methanol (6.4 ml). The solution was concentrated to about 6 ml and cooled to 5° C. The resulting solid was filtered and washed with cold methanol to give 34 as red crystals: 10.9 g Yield: 94% $^1$H NMR spectrum (DMSOd$_6$): 1.89 (m, 4H); 3.30 (m, 4H); 3.67 (s, 3H); 3.72 (s, 6H); 5.80 (d, 1H); 6.43 (d, 1H); 6,47 (s, 2H); 7.27 (d, 1H); 7.64 (d, 1H); 7.88 (d, 1H).

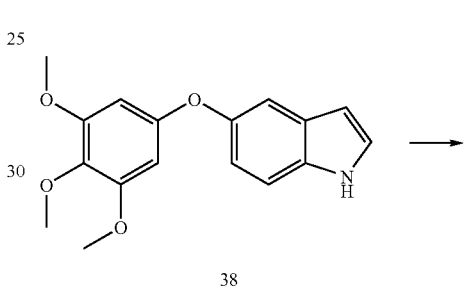

34

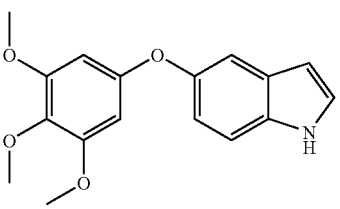

38

5-(3,4,5-Trimethoxyphenoxy)-1H-indole

To a stirred solution of 34 (10.9 g; 27.25 mmol) in THF (48 ml) and MeOH (48 ml) at 30° C. under argon was added excess Raney nickel followed by hydrazine hydrate 85% (2.9 ml). Vigorous gas evolution was observed and temperature rose to 46° C. An additional 2.9 ml of hydrazine hydrate was added 1 hr later. The temperature was maintained between 45–50° C. for 2 h after the last addition. The catalyst was removed by filtration on celite and was washed several times with $CH_2Cl_2$; after evaporation of the filtrate, the residue was purified by flash chromatography, eluting with AcOEt/Essence G 4:6 then 1:1 to give 38 as a white solid: 3.5 g Yield: 43%. $^1$H NMR spectrum (DMSOd$_6$): 3.63 (s,3H); 3.68 (s,6H); 6.26 (s, 2H); 6.41 (d, 1H); 6.83 (dd, 1H); 7.19 (d, 1H); 7.36 (m, 2H); 11.12 (s, 1H).

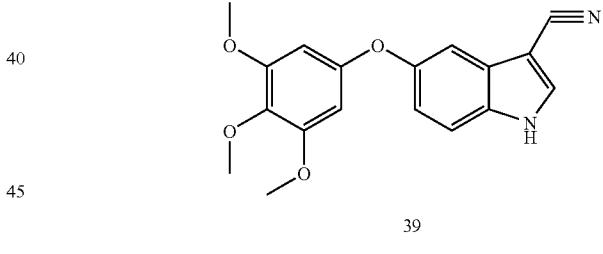

3-Cyano-5-(3,4,5-trimethoxyphenoxy)-1H-indole 38 (2.3 g; 7.69 mmol) in solution in $CH_3CN$ (7 ml) and $Et_2O$ (10 ml) was treated with Chlorosulfonyl isocyanate (1.33 ml; 15.38 mmol). After stirring for 1 hour, the solvents were removed and the residue was triturated several times in pentane, dried under vacuum and then taken up in DMF (30 ml); the solution was stirred at room temperature for 1 hr and poured in cold water. The resulting precipitate was filtrated, dried and purified by flash chromatography on silica gel, eluting with $CH_2Cl_2/Et_2O$ 1:1 to give 39 as a white solid: 2.02 g Yield: 81%. $^1$H NMR spectrum (DMSOd$_6$): 3.65 (s,3H); 3.71 (s,6H); 6.35 (s, 2H); 7.02 (dd, 1H); 7.18 (d, 1H); 7.56 (d, 1H); 8.26 (s, 1H).

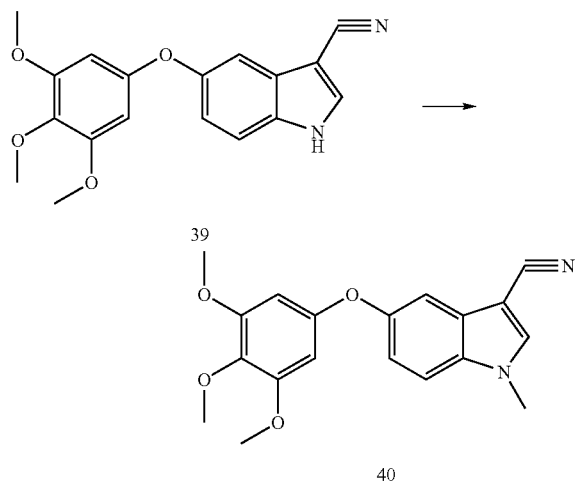

39

40

1-Methyl-3-cyano-5-(3,4,5-trimethoxyphenoxy)-1H-indole 39 (230 mg; 0.71 mmol) in solution in DMF (0.9 ml) was treated with NaH 60% dispersed in mineral oil (33 mg; 0.71 mmol). The mixture was stirred under argon atmosphere for 10 mn and CH$_3$I (73 µl; 0.78 mmol) was added. The mixture was stirred under argon atmosphere for 1 h and poured into cold water. The resulting white solid was filtrated washed with water and dried under vacuum for a night to give 40:230 mg.

Yield: 96% $^1$H NMR spectrum (DMSOd$_6$): 3.66 (s, 3H); 3.71 (s, 6H); 3.89 (s, 3H); 6.35 (s, 2H); 7.10 (dd, 1H); 7.19 (d, 1H); 7.68 (d, 1H); 8.26 (s, 1H).

EXAMPLE 19

1-Methyl-3-cyano-5-(4-phosphonoxy-3,5-dimethoxyphenoxy)-1H-indole

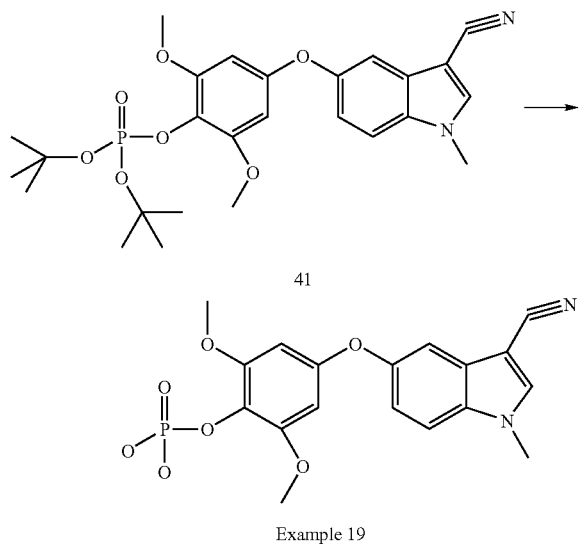

41

Example 19

41 (470 mg; 0.91 mmol) in solution in CH$_2$Cl$_2$ (1 ml) was treated under argon with a 2N HCl in dioxan (6.5 ml). The mixture was stirred at room temperature for 2 hr, evaporated and the residue was purified by crystallisation in Et$_2$O/pentane: 250 mg Yield: 68%

| Elemental analysis | Found | C 51.00 | H 4.45 | N 6.50 |
|---|---|---|---|---|
| C$_{18}$H$_{17}$N$_2$O$_7$P, H$_2$O | Requires | C 51.19 | H 4.53 | N 6.63 |

The starting material 41 was prepared as follows:

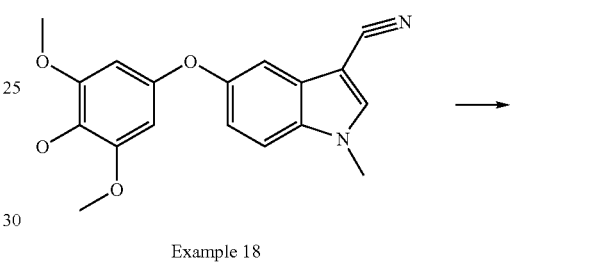

Example 18

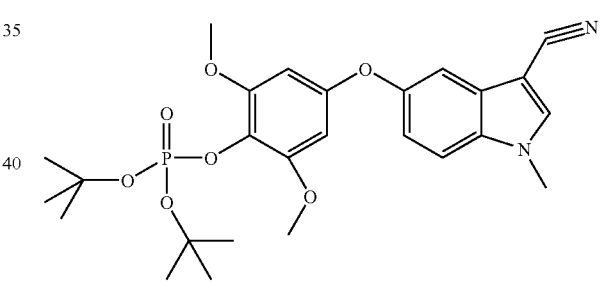

41

1-Methyl-3-cyano-5-[4-(di-tert-butylphosphonoxy)-3,5-dimethoxyphenoxy]-1H-indole To a solution of M584994 (870 mg; 2.68 mmol) in THF (4 ml) was added tetrazole (376 mg; 5.37 mmol) and di-tert-butyl-N,N-diethylphosphoramidate (900 µl; 3.22 mmol). The mixture was stirred at room temperature for 2 hr, cooled to −40° C. and a solution of MCPBA (659 mg; 2.95 mmol) in CH$_2$Cl$_2$ (5 ml) was added. After stirring at 0° C. for 1 h, the mixture was poured on cold water, washed with NaHSO$_3$ and extracted with CH$_2$Cl$_2$. The organic phase was washed with cold 2N NaOH and evaporated. The residue was purified by flash chromatography on silica gel, eluting with CH$_2$Cl$_2$/AcOEt 8:2 then with CH$_2$Cl$_2$/AcOEt/Acetone 8:1.5:0.5 to give 5:471 mg Yield: 33.6% $^1$H NMR spectrum (DMSOd$_6$): 1.45 (s, 18H); 3.70 (s, 6H); 3.89 (s, 3H); 6.39 (s, 2H); 7.11 (dd, 1H); 7.18 (s, 1H); 7.70 (d, 1H); 8.27 (s, 1H)

EXAMPLE 20

2-Carbamoyl-5-(2,5-dimethoxybenzyloxy)-1H-indole

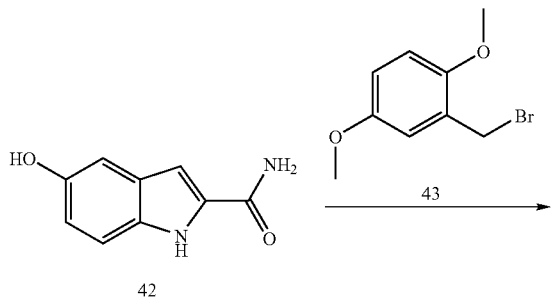

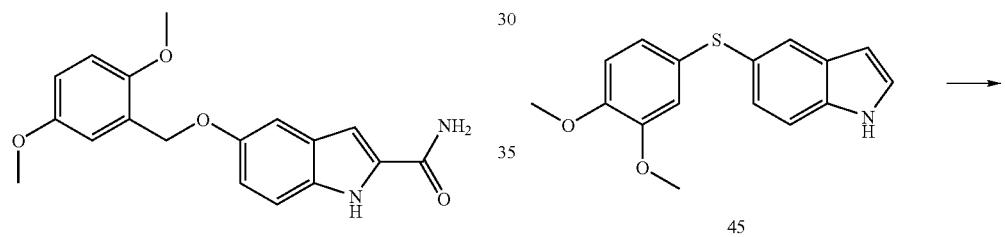

Example 20

A mixture of 42 (0.265 g; 1.5 mmol), 43 (0.381 g; 1.65 mmol) and Cs$_2$CO$_3$ (0.536 g; 1.65 mmol) in acetonitrile (20 ml) was heated at 90° C. under argon atmosphere for 2 hours. After evaporation to dryness the residue was purified by flash chromatography eluting with a 0–30% gradient of acetone/CH$_2$Cl$_2$ to give the title compound.

Yield: 24% $^1$H NMR Spectrum (DMSOd$_6$): 3.69 (s, 3H); 3.74 (s, 3H); 5.02 (s, 2H); 6.8–6.93 (m, 3H); 6.95–7.08 (m, 2H); 7.12 (d, 1H); 7.28 (s, 1H); 7.30 (d, 1H); 7.88 (s, 1H); 11.36 (s, 1H). MS-ESI: 327 [M+H]$^+$ The starting material was prepared as follows:

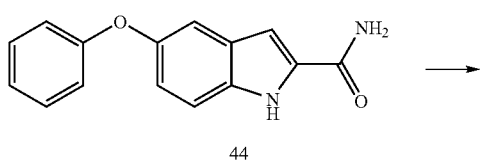

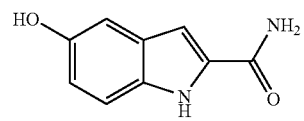

2-Carbamoyl-5-hydroxy-1H-indole

A solution of 44 (1 g; 3.35 mmol) in Methanol (60 ml) was hydrogenated under medium pressure (45 psi) over 10% palladium on carbon (0.5 g) for 2 hours. After filtration of the catalyst on celite, the filtrate was evaporated to dryness to give 42 which was used without further purification.

Yield: 95% $^1$H NMR Spectrum (DMSOd$_6$): 6.71–6.74 (m, 1H); 6.8–6.95 (m, 2H); 7.1–7.3 (m, 2H); 7.83 (broad, 1H); 8.78 (broad, 1H); 11.21 (s, 1H).

EXAMPLE 21

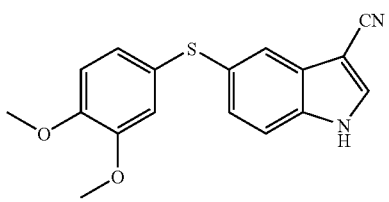

Example 21

A solution of chlorosulfonyl isocyanate (0.365 ml; 4.2 mmol) in acetonitrile (1.5 ml) was added at 0° C. to a solution of 45 (1.2 g; 4.2 mmol) in acetonitrile (12 ml). The mixture was stirred under argon atmosphere for 1 hour at 0° C. A solution of triethylamine (0.571 ml) in acetonitrile (3 ml) was then added at 0° C.; the mixture was allowed to warm up and stirred at room temperature for 3 hours. After evaporation the residue was taken up in CH$_2$Cl$_2$. The organic phase was washed with diluted NaHCO$_3$, evaporated and purified by flash chromatography eluting with CH$_2$Cl$_2$ to give the title compound.

Yield: 52% MS-ESI: 311 [M+H]$^+$ $^1$H NMR Spectrum (DMSOd$_6$): 3.72 (s, 3H); 3.77 (s, 3H); 6.93–7.023 (m, 3H); 7.22 (d, 1H); 7.53 (m, 2H); 8.28 (s, 1H); 12.0 (s, 1H).

The starting material was prepared as follows

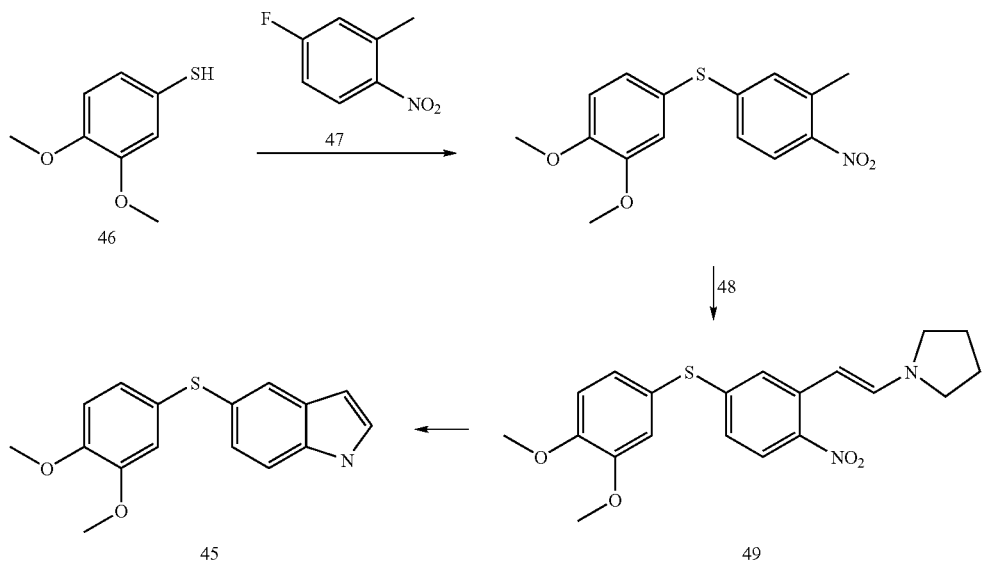

2-Methyl-4-(3,4-dimethoxyphenylsulphanyl)-nitrobenzene

To a solution of 46 (3.4 g; 20 mmol) and 47 (3.10 g; 30 mmol) in NMP (40 ml) was added $K_2CO_3$ (4.14 g; 30 mmol). The mixture was stirred at 80° C. for 2 hours under argon atmosphere. After extraction with a mixture of Ether/Ethylacetate, the organic phase was evaporated and purified by flash chromatography, eluting with petroleum ether and petroleum ether/ethylacetate 7:3 to give 48.

Yield: 83% $^1$H NMR Spectrum (DMSOd$_6$): 2.48 (s, 3H); 3.74 (s, 3H); 3.77 (s, 3H); 6.97 (dd, 1H); 7.10–7.20 (m, 4H); 7.9 (d, 1H).

2-(pyrrolidine-1-ylpropanyl-2-ylidene-4-(3,4-dimethoxyphenylsulphanyl)-nitrobenzene To a solution of 48 (5.1 g; 16.7 mmol) in DMF (9 ml) was added N,N-dimethylformamide dimethylacetal (2.57 ml; 19.3 mmol) and pyrrolidine (1.61 ml; 19.3 mmol). The mixture was heated at reflux under argon atmosphere for 3 hours. After extraction with AcOEt, the organic phase was evaporated to give 49 which was used in the next step without purification.

Yield: 92%.

5-(3,4-Dimethoxyphenylsulphanyl)-1H-indole

To a solution of 49 (5.9 g; 15.2 mmol) in MeOH/THF (30 ml/30 ml) was added Raney Nickel (3 g). The mixture was heated at 48° C., under argon atmosphere and a solution of hydrazine hydrate (1.52 g; 30.4 mmol) in THF/MeOH 30 ml/30 ml was added dropwise. After heating at 48° C. for 2 hours, the mixture was filtered on celite. The filtrate was evaporated and purified by flash chromatography eluting with AcOEt/petroleum ether 30/70 to give 45.

Yield: 35% $^1$H NMR Spectrum: 3.69 (s, 3H); 3.73 (s, 3H); 6.43 (s, 1H); 6.77 (dd, 1H); 6.90–6.92 (m, 2H); 7.11 (dd, 1H); 7.39 (m, 2H); 7.64 (s, 1H); 11.25 (s, 1H).

EXAMPLE 22

1-Methyl-3-cyano-5-(3,4-dimethoxyphenylsulphanyl)-1H-indole

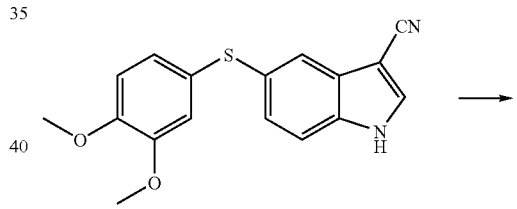

Example 21

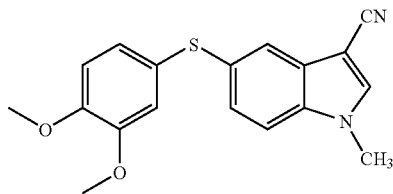

Example 22

To a solution of Example 21 (0.2 g; 0.64 mmol) in DMF (0.8 ml) at 0° C. was added NaH (0.03 g; 0.64 mmol) and $CH_3I$ (0.06 ml; 0.64 mmol). The mixture was stirred at ambient temperature for 2 hours. After extraction with AcOEt the organic phase was evaporated and purified by flash chromatography eluting with petroleum ether/AcOEt 60/40 to give the title compound.

Yield: 77% $^1$H NMR Spectrum (DMSOd$_6$): 3.72 (s, 3H); 3.77 (s, 3H); 3.87 (s, 3H); 6.98–7.03 (m, 3H); 7.30 (dd, 1H); 7.52 (s, 1H); 7.63 (d, 1H); 8.28 (s, 1H). MS-ESI: 325 [M+H]$^+$

EXAMPLE 23

3-Cyano-5-(3,4-dimethoxyphenylsulphonyl)-1H-indole

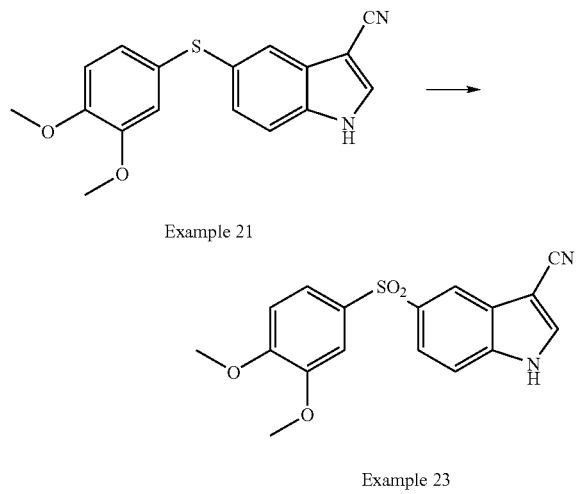

Example 21

Example 23

To a solution of Example 21 (0.13 g; 0.42 mmol) in CH$_2$Cl$_2$ (10 ml) and CH$_3$CN (2 ml) was added a solution of MCPBA (0.19 g; 0.88 mmol) in chloroform (5 ml). The mixture was heated at ambient temperature for one hour. After evaporation to dryness, the solid was triturated in ether and dried to give the title compound.

Yield: 59% $^1$H NMR (DMSOd$_6$): 3.82 (s, 3H); 3.84 (s, 3H); 7.15 (d, 1H); 7.45 (d, 1H); 7.61 (dd, 1H); 7.73 (d, 1H); 7.81 (dd, 1H); 8.25 (s, 1H); 8.48 (s, 1H). MS-ESI: 341 [M–H]$^-$

EXAMPLE 24

1-Methyl-3-cyano-5-(3,4-dimethoxyphenylsulpho-nyl)-1H-indole

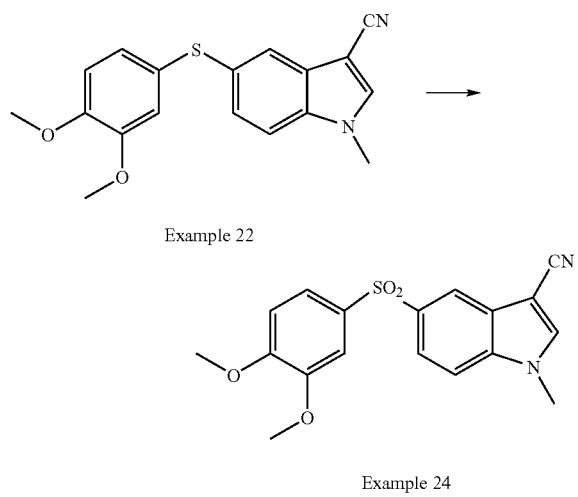

Example 22

Example 24

The compound was prepared following the method described for example 23 but starting with compound of example 22.

Yield: 77%. $^1$H NMR (DMSOd$_6$): 3.78 (s, 3H); 3.82 (s, 3H); 3.91 (s, 3H); 7.13 (d, 1H); 7.46 (s, 1H); 7.60 (dd, 1H); 7.84–7.91 (m, 2H); 8.25 (s, 1H); 8.48 (s, 1H). MS-ESI: 357 [M+H]$^+$

What is claimed is:

1. A compound of Formula (VIId),

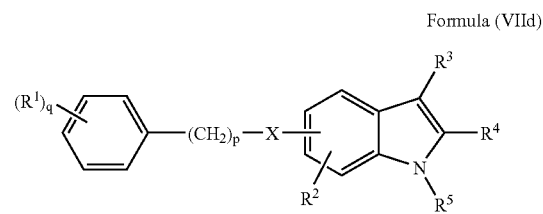

Formula (VIId)

wherein

R$^1$ is independently selected from hydroxy, amino, alkanoylamino, —OPO$_3$H$_2$, or C$_{1-4}$alkoxy, wherein the amino group is optionally substituted with an amino acid residue and the hydroxy group is optionally esterified;

X is selected from —O—, —S—, —SO—, or —SO$_2$—;

R$^2$ is selected from hydrogen, C$_{1-4}$alkyl, C$_{1-4}$alkoxy;

R$^4$ is independently selected from hydrogen, C$_{1-4}$alkyl, $_{1-4}$alkanoyl, C$_{1-4}$alkoxycarbonyl, C$_{1-4}$alkoxycarbonylC$_{1-4}$alkyl, aminoC$_{1-4}$alkyl, carbamoyl, carbamoylC$_{1-4}$alkyl, cyano, cyanoC$_{1-4}$alkyl, hydroxy or hydroxyC$_{1-4}$alkyl;

R$^5$ is selected from hydrogen, C$_{1-4}$alkyl, or a group of Formula (III)

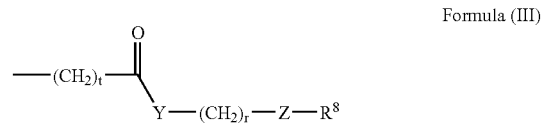

Formula (III)

wherein

Y is selected from —NH—, —O—, or a bond;

Z is selected from —NH—, —O—, —C(O)— or a bond;

r is an integer from 0 to 4;

t is an integer from 0 to 1;

R$^8$ is hydrogen, C$_{1-4}$alkyl, C$_{1-4}$alkoxy, aryl, 5- or 6-membered heterocyclyl, 5- or 6-membered heteroaryl, wherein aryl, heteroaryl or heterocyclyl are optionally substituted with C$_{1-4}$alkyl, C$_{1-4}$alkoxy, or a group of Formula (IV)

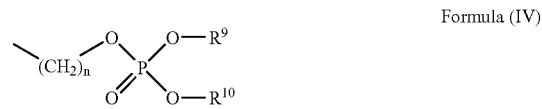

Formula (IV)

wherein n is an integer from 1 to 6, and;

R$^9$ and R$^{10}$ are independently selected from hydrogen, C$_{1-4}$alkyl or aryl;

p is an integer from 0 to 1 and q is an integer from 1 to 3;

or a salt, or solvate thereof.

2. A compound of claim 1, selected from:
3-cyano-5-(4-hydroxyphenoxy)-1H-indole; and
1-methyl-3-cyano-5-(4-hydroxy-3,5-dimethoxyphenoxy)-1H-indole;
1-methyl-3-cyano-5-(4-phosphonoxy-3,5-dimethoxyphenoxy)-1H-indole;
3-cyano-5-(3,4-dimethoxyphenylsulphanyl)-1H-indole;
1-methyl-3-cyano-5-(3,4-dimethoxyphenylsulphanyl)-1H-indole;
3-cyano-5-(3,4-dimethoxyphenylsulphonyl)-1H-indole; and
1-methyl-3-cyano-5-(3,4-dimethoxyphenylsulphonyl)-1H-indole;
or salt, or solvate thereof.

3. A compound according to claim 1 wherein X is —O—.

4. A compound according to claim 1 wherein X is —S—, —SO— or —SO$_2$—.

5. A compound according to claim 1 wherein $R^1$ is selected from hydroxy, amino, —OPO$_3$H$_2$, methoxy, ethoxy, glutamylamino, α-glutamylamino, serylamino, glycylamino and alanylamino.

6. A compound according to claim 1 wherein $R^1$ is selected from hydroxy, α-glutamylamino, seryl, —OPO$_3$H$^2$ or methoxy.

7. A compound according to claim 1 wherein q is 2 or 3.

8. A compound according to claim 1 wherein $R^2$ is hydrogen.

9. A compound according to claim 1 wherein $R^4$ is hydrogen, cyano, carbamoyl, carbamoylC$_{1-4}$alkyl or C$_{1-4}$alkoxycarbonyl.

10. A compound according to claim 1 wherein $R^5$ is hydrogen or C$_{1-4}$alkyl.

11. A compound according to claim 1 wherein $R^5$ is hydrogen, methyl or ethyl.

12. A pharmaceutical composition comprising a compound according to any one of claims 1, 2, 3 to 11 or a pharmaceutically acceptable salt, or solvate or thereof.

13. A process for preparing a compound of claim 1, or salt, or solvate thereof, comprising
a) for compounds of Formula (I) wherein X is —O— or —S—, reacting a compound of Formula (A) with a compound of Formula (B),

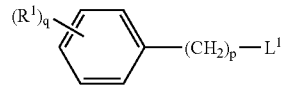

Formula (A)

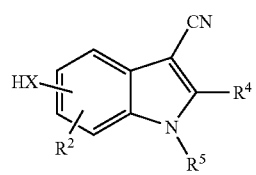

Formula (B)

wherein $L^1$ is a leaving group;
b) for compounds of Formula (I) in which $R^-$ is amino, reduction of a compound of Formula (C):

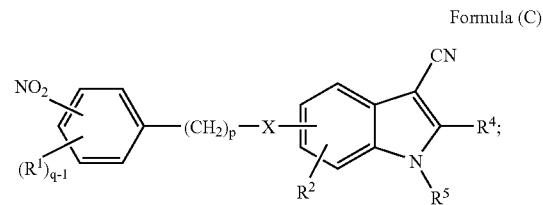

Formula (C)

c) for compounds of Formula (I) wherein $R^5$ is C$_{1-4}$alkyl, reacting a compound of Formula (I) wherein $R^5$ is hydrogen with a suitable alkylhalide;
d) for compounds of Formula (I) wherein $R^1$ comprises an amino group substituted with an amino acid residue, reacting a compound of Formula (D) with an amino acid,

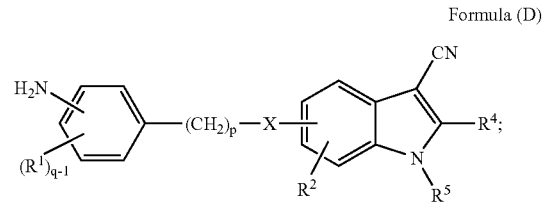

Formula (D)

e) for compounds of Formula (I) in which $R^4$ is hydrogen, reacting compounds of Formula (I) in which $R^3$ is hydrogen and $R^4$ is hydrogen with compounds of L$^3$R$^3$ in which $L^3$ is a leaving group ; and
f) for compounds of Formula (I) in which $R^1$ is an esterified hydroxyl group, reacting a compound of Formula (F) with ar appropriate carboxylic acid or carboxylic acid derivative;

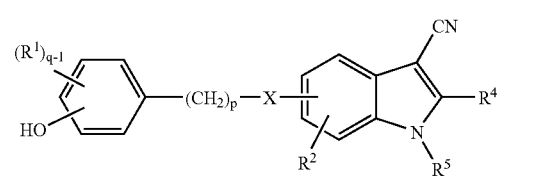

Formula (F)

and thereafter optionally
  i) converting a compound of Formula (I) into another compound of Formula (I);
  ii) removing any protecting groups;
  iii) forming a salt, or solvate.

* * * * *